US006083923A

United States Patent [19]

Hardee et al.

[11] Patent Number: 6,083,923

[45] Date of Patent: *Jul. 4, 2000

[54] LIPOSOMAL OLIGONUCLEOTIDE COMPOSITIONS FOR MODULATING RAS GENE EXPRESSION

[75] Inventors: Gregory E. Hardee, Rancho Sante Fe; Richard S. Geary, Carlsbad; Arthur Levin, Rancho Sante Fe; Michael V. Templin, Carlsbad; Randy Howard, Encinitas; Rahul C. Mehta, San Marcos, all of Calif.

[73] Assignee: Isis Pharmaceuticals Inc., Carlsbad, Calif.

[ * ] Notice: This patent is subject to a terminal disclaimer.

[21] Appl. No.: 08/961,469

[22] Filed: Oct. 31, 1997

[51] Int. Cl.$^7$ .......................... A61K 48/00; C07H 21/04; C07H 21/02; C12N 15/11

[52] U.S. Cl. .............................. 514/44; 435/6; 435/455; 435/375; 435/377; 536/23.1; 536/24.1; 536/24.5

[58] Field of Search .............................. 435/6, 375, 377, 435/455; 536/23.1, 24.1, 24.5; 514/44

[56] References Cited

U.S. PATENT DOCUMENTS

| | | | |
|---|---|---|---|
| 4,426,330 | 1/1984 | Sears | 260/403 |
| 4,534,899 | 8/1985 | Sears | 260/403 |
| 4,837,028 | 6/1989 | Allen | 424/450 |
| 5,013,556 | 5/1991 | Woodle et al. | 424/450 |
| 5,213,804 | 5/1993 | Martin et al. | 424/450 |
| 5,225,212 | 7/1993 | Martin et al. | 424/450 |
| 5,264,221 | 11/1993 | Tagawa et al. | 424/450 |
| 5,356,633 | 10/1994 | Woodle et al. | 424/450 |
| 5,527,528 | 6/1996 | Allen et al. | 424/178.1 |
| 5,540,935 | 7/1996 | Miyazaki et al. | 424/450 |
| 5,543,152 | 8/1996 | Webb et al. | 424/450 |
| 5,556,948 | 9/1996 | Tagawa et al. | 530/391.9 |
| 5,576,208 | 11/1996 | Monia et al. | 435/240.2 |
| 5,582,972 | 12/1996 | Lima et al. | 435/6 |
| 5,582,986 | 12/1996 | Monia et al. | 435/6 |
| 5,593,974 | 1/1997 | Rosenberg et al. | 514/44 |
| 5,661,134 | 8/1997 | Cook et al. | 514/44 |
| 5,665,710 | 9/1997 | Rahman et al. | 514/44 |

FOREIGN PATENT DOCUMENTS

| | | |
|---|---|---|
| 0 445 131 B1 | 10/1989 | WIPO . |
| WO 90/04384 | 5/1990 | WIPO . |
| 0 496 813 B1 | 10/1990 | WIPO . |
| WO 91/05545 | 5/1991 | WIPO . |
| WO 92/22651 | 12/1992 | WIPO . |
| WO 94/08003 | 4/1994 | WIPO . |
| WO 94/20073 | 9/1994 | WIPO . |
| WO 96/10391 | 4/1996 | WIPO . |
| WO 96/40062 | 12/1996 | WIPO . |
| WO 97/04787 | 2/1997 | WIPO . |

OTHER PUBLICATIONS

Uhlmann et al. "Antisense Oligonucleotides: A New Therapeutic Principle" Chemical Reviews vol. 90(4):543–584, Jun. 1990.

Agrawal, S. "Antisense Oligonucleotides: Towards Clinical Trials" TIBTECH vol. 14:376–387, Oct. 1996.

Branch, A. "A Good Antisense is Hard to Find" TIBS vol. 23:45–50, Feb. 1998.

Chang et al. "Antisense Inhibition of ras p21 Expression that is Sensitive to a Point Mutation" Biochemistry vol. 30(34):8283–8286, Aug. 27, 1991.

Allen et al., "Large unilamellar liposomes with low uptake into the reticuloendothelial system", *FEBS Letters* 223:42, 1987.

Blume et al., "Liposomes for the sustained drug release in vivo", *Biochimica et Biophysica Acta* 1029:91, 1990.

Chonn et al., "Recent advances in liposomal drug–delivery systems", *Current Op. Biotech.* 6:698, 1995.

Cossum et al., "Disposition of the $^{14}$C–Labeled Phosphorothioate Oligonucleotide ISIS 2105 after Intravenous Administration to Rats", *J. Pharmacol. Exp. Therap.* 267:1181, 1993.

Dean et al., "Inhibition of Growth of Human Tumor Cell Lines in Nude Mice by an Antisense Oligonucleotide Inhibitor of Protein Kinase C–α Expression" *Cancer Res.* 56:3499, 1996.

Dean et al., "Inhibition of protein kinase C–α expression in mice after systemic administration of phosphorothioate antisense oligodeoxynucleotides", *Proc. Natl. Acad. Sci. U.S.A.* 91:11766, 1994.

Downward, "The ras superfamily of small GTP–binding proteins", *Trends Biochem. Sci.* 15:469, 1990.

Gabizon et al., "Liposome formulations with prolonged circulation time in blood and enhanced uptake by tumors", *Proc. Natl. Acad. Sci. U.S.A.* 85:6949, 1988.

Illum et al., "The organ uptake of intravenously administered colloidal particles can be altered using a non–ionic surfactant (Poloxamer 338)", *FEBS Letters* 167:79, 1984.

Klibanov et al., "Amphipathic polyethyleneglycols effectively prolong the circulation time of liposomes", *FEBS Letts.* 268:235, 1990.

Marshall, "The effector interactions of p21$^{ras}$", *Trends Biochem. Sci.* 18:250, 1993.

Papahadjopoulos et al., "Targeting of Liposomes to Tumor Cells in Vivoα", *Ann. N.Y. Acad. Sci.,* 308:64, 1978.

Papahadjopoulos et al., "Sterically stabilized liposomes: Improvements in pharmacokinetics and antitumor therapeutic efficacy", *Proc. Natl. Acad. Sci. U.S.A.* 88:11460, 1991.

Sunamoto et al., Liposomal Membranes. V. Interaction of Zinc(II) Ion with Egg Phosphatidylcholine Liposomes, *Bull. Chem. Soc. Jpn.* 53:2778, 1980.

Weinberg, "How Cancer Arises", *Sci. American* 275:62 1996.

(List continued on next page.)

*Primary Examiner*—Nancy Degen
*Assistant Examiner*—Sean McGarry
*Attorney, Agent, or Firm*—Law Offices of Jane Massey Licata

[57] ABSTRACT

Pharmaceutical compositions comprising sterically stabilized liposomes containing antisense oligonucleotides are provided for the modulation of expression of the human ras gene in both the normal (wildtype) and activated (mutant) forms.

4 Claims, 7 Drawing Sheets

OTHER PUBLICATIONS

Wu et al., "Increased Microvascular Permeability Contributes to Preferential Accumulation of Stealth[1] Liposomes in Tumor Tissue[2]", *Cancer Research* 53:3765, 1993.

Agrawal et al., "Pharmacokinetics of Antisense Oligonucleotides", *Clinical Pharmacokinet.* 28:7, 1995.

Davies et al., "Physiological Parameters in Laboratory Animals and Humans", *Pharm. Res.* 10:1093, 1993.

SEQUENCE LISTING (1) GENERAL INFORMATION:

(iii) NUMBER OF SEQUENCES: 61

(2) INFORMATION FOR SEQ ID NO: 1:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 1:

CTTATATTCC GTCATCGCTC                                    20

(2) INFORMATION FOR SEQ ID NO: 2:

(i) SEQUENCE CHARACTERISTICS:
       (A) LENGTH: 20
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 2:

TCCGTCATCG CTCCTCAGGG                                    20

(2) INFORMATION FOR SEQ ID NO: 3:

(i) SEQUENCE CHARACTERISTICS:
       (A) LENGTH: 17
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 3:

CCACACCGAC GGCGCCC                                       17

(2) INFORMATION FOR SEQ ID NO: 4:

(i) SEQUENCE CHARACTERISTICS:
       (A) LENGTH: 19
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 4:

CCCACACCGA CGGCGCCCA                                    19

(2) INFORMATION FOR SEQ ID NO: 5:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 5:

-continued

```
GCCCACACCG ACGGCGCCCA C                                              21

(2) INFORMATION FOR SEQ ID NO: 6:

(i) SEQUENCE CHARACTERISTICS:
          (A) LENGTH: 23
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 6:

TGCCCACACC GACGGCGCCC ACC                                            23

(2) INFORMATION FOR SEQ ID NO: 7:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 7:

TATTCCGTCA TCGCTCCTCA                                                20

(2) INFORMATION FOR SEQ ID NO: 8:

(i) SEQUENCE CHARACTERISTICS:
          (A) LENGTH: 5
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 8:

CGACG                                                                 5

(2) INFORMATION FOR SEQ ID NO: 9:

(i) SEQUENCE CHARACTERISTICS:
          (A) LENGTH: 7
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 9:

CCGACGG                                                               7

(2) INFORMATION FOR SEQ ID NO: 10:

(i) SEQUENCE CHARACTERISTICS:
          (A) LENGTH: 9
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 10:

ACCGACGGC                                                             9

(2) INFORMATION FOR SEQ ID NO: 11:
```

(i) SEQUENCE CHARACTERISTICS:
        (A) LENGTH: 11
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

CACCGACGGC G                                                                11

(2) INFORMATION FOR SEQ ID NO: 12:

(i) SEQUENCE CHARACTERISTICS:
        (A) LENGTH: 13
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

ACACCGACGG CGC                                                              13

(2) INFORMATION FOR SEQ ID NO: 13:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 13:

CACACCGACG GCGCC                                                            15

(2) INFORMATION FOR SEQ ID NO: 14:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

CCACACCGAC GGCGCC                                                           16

(2) INFORMATION FOR SEQ ID NO: 15:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

CACACCGACG GCGCCC                                                           16

(2) INFORMATION FOR SEQ ID NO: 16:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 16:

CCCACACCGA CGGCGCCC                                                        18

(2) INFORMATION FOR SEQ ID NO: 17:

(i) SEQUENCE CHARACTERISTICS:
                (A) LENGTH: 18
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 17:

CCACACCGAC GGCGCCCA                                                        18

(2) INFORMATION FOR SEQ ID NO: 18:

(i) SEQUENCE CHARACTERISTICS:
                (A) LENGTH: 25
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 18:

TTGCCCACAC CGACGGCGCC CACCA                                                25

(2) INFORMATION FOR SEQ ID NO: 19:

(i) SEQUENCE CHARACTERISTICS:
                (A) LENGTH: 17
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 19:

CCACACCGCC GGCGCCC                                                         17

(2) INFORMATION FOR SEQ ID NO: 20:

(i) SEQUENCE CHARACTERISTICS:
                (A) LENGTH: 10
                (B) TYPE: nucleic acid
                (C) STRANDEDNESS: Single
                (D) TOPOLOGY: Linear (iv) ANTI-SENSE: YES (xi) SEQUENCE DESCRIPTION: SEQ ID NO: 20:

CACCACCACC                                                                 10

(2) INFORMATION FOR SEQ ID NO: 21:

(i) SEQUENCE CHARACTERISTICS:
                (A) LENGTH: 10
                (B) TYPE: nucleic acid
                (C) STRANDEDNESS: Single
                (D) TOPOLOGY: Linear (iv) ANTI-SENSE: YES (xi) SEQUENCE DESCRIPTION: SEQ ID NO: 21:

GCGCCCACCA 10

(2) INFORMATION FOR SEQ ID NO: 22:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: YES (xi) SEQUENCE DESCRIPTION: SEQ ID NO: 22:

CGACGGCGCC 10

(2) INFORMATION FOR SEQ ID NO: 23:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: YES (xi) SEQUENCE DESCRIPTION: SEQ ID NO: 23:

CACACCGACG 10

(2) INFORMATION FOR SEQ ID NO: 24:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: YES (xi) SEQUENCE DESCRIPTION: SEQ ID NO: 24:

UUGCCCACAC 10

(2) INFORMATION FOR SEQ ID NO: 25:

(i) SEQUENCE CHARACTERISTICS:
        (A) LENGTH: 10
        (B) TYPE: nucleic acid
        (C) STRANDEDNESS: Single
        (D) TOPOLOGY: Linear (iv) ANTI-SENSE: NO (xi) SEQUENCE DESCRIPTION: SEQ ID NO: 25:

CACUCUUGCC 10

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: Single
        (D) TOPOLOGY: Linear (iv) ANTI-SENSE: YES (xi) SEQUENCE DESCRIPTION: SEQ ID NO: 26:

TCAGTAATAG CCCCACATGG 20

(2) INFORMATION FOR SEQ ID NO: 27:

(i) SEQUENCE CHARACTERISTICS:
            (A) LENGTH: 20
            (B) TYPE: nucleic acid
            (C) STRANDEDNESS: Single
            (D) TOPOLOGY: Linear (iv) ANTI-SENSE: YES (xi) SEQUENCE DESCRIPTION: SEQ ID NO: 27:

TTGCTTCCAT CTTCCTCGTC                                                         20

(2) INFORMATION FOR SEQ ID NO: 28:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 28:

CTGCCTCCGC CGCCGCGGCC                                                         20

(2) INFORMATION FOR SEQ ID NO: 29:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 29:

CAGTGCCTGC GCCGCGCTCG                                                         20

(2) INFORMATION FOR SEQ ID NO: 30:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 30:

AGGCCTCTCT CCCGCACCTG                                                         20

(2) INFORMATION FOR SEQ ID NO: 31:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 31:

TTCAGTCATT TTCAGCAGGC                                                         20

(2) INFORMATION FOR SEQ ID NO: 32:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 32:

TTATATTCAG TCATTTTCAG                                                    20

(2) INFORMATION FOR SEQ ID NO: 33:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 33:

CAAGTTTATA TTCAGTCATT                                                    20

(2) INFORMATION FOR SEQ ID NO: 34:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 34:

GCCTACGCCA CCAGCTCCAA C                                                  21

(2) INFORMATION FOR SEQ ID NO: 35:

(i) SEQUENCE CHARACTERISTICS:
            (A) LENGTH: 17
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 35:

CTACGCCACC AGCTCCA                                                       17

(2) INFORMATION FOR SEQ ID NO: 36:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 36:

GTACTCCTCT TGACCTGCTG T                                                  21

(2) INFORMATION FOR SEQ ID NO: 37:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 37:

CCTGTAGGAA TCCTCTATTG T                                     21

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

GGTAATGCTA AAACAAATGC                                        20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

GGAATACTGG CACTTCGAGG                                        20

(2) INFORMATION FOR SEQ ID NO: 40:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

TACGCCAACA GCTCC                                             15

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

TTTTCAGCAG GCCTCTCTCC                                        20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 42:

CCGGGTCCTA GAAGCTGCAG                                        20

(2) INFORMATION FOR SEQ ID NO: 43:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 43:

TAAATCAGTA AAAGAAACCG                                               20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

GGACACAGTA ACCAGGCGGC                                               20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

AACAGAAGCT ACACCAAGGG                                               20

(2) INFORMATION FOR SEQ ID NO: 46:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

CAGACCCATC CATTCCCGTG                                               20

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

GCCAAGAAAT CAGACCCATC                                               20

(2) INFORMATION FOR SEQ ID NO: 48:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

AGGGGGAAGA TAAAACCGCC                                                   20

(2) INFORMATION FOR SEQ ID NO: 49:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 49:

CGCTTCCATT CTTTCGCCAT                                                   20

(2) INFORMATION FOR SEQ ID NO: 50:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 50:

CCGCACCCAG ACCCGCCCCT                                                   20

(2) INFORMATION FOR SEQ ID NO: 51:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 51:

CAGCCCCCAC CAAGGAGCGG                                                   20

(2) INFORMATION FOR SEQ ID NO: 52:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 52:

GTCATTTCAC ACCAGCAAGA                                                   20

(2) INFORMATION FOR SEQ ID NO: 53:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 53:

CAGTCATTTC ACACCAGCAA 20

(2) INFORMATION FOR SEQ ID NO: 54:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 54:

CTCAGTCATT TCACACCAGC 20

(2) INFORMATION FOR SEQ ID NO: 55:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 55:

CGTGGGCTTG TTTTGTATCA 20

(2) INFORMATION FOR SEQ ID NO: 56:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 56:

CCATACAACC CTGAGTCCCA 20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 57:

CAGACAGCCA AGTGAGGAGG 20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 58:

CCAGGGCAGA AAAATAACAG 20

(2) INFORMATION FOR SEQ ID NO: 59:

-continued

```
    (i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 59:

TTTGTGCTGT GGAAGAACCC                                               20

(2) INFORMATION FOR SEQ ID NO: 60:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 60:

GCTATTAAAT AACAATGCAC                                               20

(2) INFORMATION FOR SEQ ID NO: 61:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 61:

ACTGATCACA GCTATTAAAT                                               20
```

LIPOSOMAL OLIGONUCLEOTIDE COMPOSITIONS FOR MODULATING RAS GENE EXPRESSION

FIELD OF THE INVENTION

This invention relates to pharmaceutical compositions comprising sterically stabilized liposomes containing one or more antisense oligonucleotides. The antisense oligonucleotides contained within the sterically stabilized liposomes are from about 8 to about 30 nucleotides in length, are targeted to a nucleic acid encoding a human wildtype or mutant ras sequence and are capable, individually and/or collectively, of modulating ras expression. In another embodiment, the sterically stabilized liposomes of the invention contain (a) one or more such antisense oligonucleotides and (b) one or more chemotherapeutic compounds which do not function by an antisense mechanism.

BACKGROUND OF THE INVENTION

Alterations in the cellular genes which directly or indirectly control cellular growth (proliferation) and differentiation are considered to be causative events leading to the development of tumors and cancers (see, generally, Weinberg, *Sci. American* 275:62, 1996). There are many families of genes presently implicated in human tumor formation. Members of one such family, the ras gene family, are frequently found to be mutated in human tumors. In their normal state, proteins produced by the ras genes are thought to be involved in normal cell growth and maturation. Mutation of the ras gene, causing an amino acid alteration at one of three critical positions in the protein product, results in conversion to a form which is implicated in tumor formation. A gene having such a mutation is said to be "activated." It is thought that such a point mutation leading to ras activation can be induced by carcinogens or other environmental factors. Over 90% of pancreatic adenocarcinomas, about 50% of adenomas and adenocarcinomas of the colon, about 50% of adenocarcinomas of the lung and carcinomas of the thyroid, and a large fraction of malignancies of the blood such as acute myeloid leukemia and myelodysplastic syndrome have been found to contain activated ras genes. Overall, some 10 to 20% of human tumors have a mutation in one of the three ras genes (H-ras, K-ras and N-ras).

It is presently believed that inhibiting expression of activated cancer-associated genes in a particular tumor cell might force the cell back into a more normal growth habit. For example, Feramisco et al. (*Nature*, 314:639, 1985) demonstrated that cells transformed to a malignant state with an activated ras gene slow their rate of proliferation and adopt a more normal appearance when microinjected with an antibody which binds to the protein product of the ras gene. This has been interpreted as support for the involvement of the product of the activated ras gene in the uncontrolled growth typical of cancer cells.

The H-ras gene has recently been implicated in a serious cardiac arrhythmia called long Q-T syndrome, a hereditary condition which often causes sudden death if treatment is not given immediately. Frequently there are no symptoms prior to the onset of the erratic heartbeat. Whether the H-ras gene is precisely responsible for long Q-T syndrome is unclear. However, there is an extremely high correlation between inheritance of this syndrome and the presence of a particular variant of the chromosome 11 region surrounding the H-ras gene. Therefore, the H-ras gene is a useful indicator of increased risk of sudden cardiac death due to the long Q-T syndrome.

There is a great desire to provide compositions of matter which can modulate the expression of the ras gene, and particularly to provide compositions of matter which specifically modulate the expression of the activated form of the ras gene. Inhibition of K-ras gene expression has been accomplished using retroviral vectors or plasmid vectors which express a 2-kilobase segment of the K-ras gene RNA in antisense orientation (Mukhopadhyay et al., *Cancer Research* 51:1744, 1991; PCT Patent Application PCT/US92/01852 (WO 92/15680). Georges et al., *Cancer Research*, 53:1743, 1993).

Antisense oligonucleotide inhibition of expression has proven to be a useful tool in understanding the role(s) of various cancer-associated gene families. Antisense oligonucleotides are small oligonucleotides which are complementary to the "sense" (coding strand) of a given gene, and are thus also complementary to, and thus able to stably and specifically hybridize with, the mRNA transcript of the gene. Holt et al. (*Mol. Cell Biol*. 8:963, 1988) state that antisense oligonucleotides designed to hybridize specifically with (i.e., "targeted to") mRNA transcripts of the c-myc gene inhibit proliferation and induce differentiation when added to cultured HL60 leukemic cells. Anfossi et al. (*Proc. Natl Acad. Sci*. 86:3379, 1989) state that antisense oligonucleotides targeted to the c-myb gene inhibit proliferation of human myeloid leukemia cell lines. Wickstrom et al. (*Proc. Nat. Acad. Sci*. 85:1028, 1988) state that expression of the protein product of the c-myc gene and proliferation of HL60 cultured leukemic cells are both inhibited by antisense oligonucleotides hybridizing specifically with c-myc mRNA.

With specific regard to oligonucleotides having ras sequences, U.S. Pat. No. 4,871,838 to Bos et al. discloses oligonucleotides complementary to a mutation in codon 13 of N-ras to detect this mutation. Helene and co-workers have reported the selective inhibition of activated (codon 12 G→T transition) H-ras mRNA expression using a 9-mer phosphodiester linked to an acridine intercalating agent and/or a hydrophobic tail; this compound displayed selective targeting of mutant ras message in both Rnase H and cell proliferation assays at low micromolar concentrations (Saison-Behmoaras et al., *EMBO J*. 10:1111, 1991). Chang et al. (*Biochemistry* 30:8283, 1991) disclose selective targeting of a mutant H-ras message, specifically, H-ras codon 61 containing an A→T transversion, with an 11-mer methylphosphonate oligonucleotide or its psoralen derivative. These compounds, which required concentrations of 7.5–150 $\mu$M for activity, were shown by immunoprecipitation to selectively inhibit mutant $p21^{H\text{-}ras}$ expression relative to wildtype $p21^{H\text{-}ras}$.

Although it has been recognized that antisense oligonucleotides have great therapeutic potential, there remains a long-felt need for pharmaceutical compositions and methods that could positively alter the in vivo stability, concentration, and distribution of such oligonucleotides. Enhanced biostability of antisense oligonucleotides in a mammal would generally be preferred for improved delivery of the oligonucleotide to its intended target tissue(s) with potentially less frequent dosing. For antisense oligonucleotides targeted to oncogenic molecules, enhanced distribution to tumor tissues would be preferred.

OBJECTS OF THE INVENTION

It is an object of the invention to provide sterically stabilized liposomes containing one or more antisense oligonucleotides and pharmaceutical compositions comprising such liposomes, wherein the antisense oligonucleotides contained within the sterically stabilized liposomes are from about 8 to about 30 nucleotides in length, are targeted to a nucleic acid encoding a human ras sequence and are capable, either individually or collectively, of modulating ras expression.

It is another object of the invention to provide sterically stabilized liposomes containing one or more antisense oligonucleotides, and pharmaceutical compositions comprising such liposomes, wherein the antisense oligonucleotides contained within the sterically stabilized liposomes are from about 8 to about 30 nucleotides in length, are targeted to a nucleic acid encoding an activated (mutant) human ras sequence and are capable, either individually or collectively, of modulating the expression of the activated form of the ras gene.

It is a further object of the invention to provide sterically stabilized liposomes containing (a) one or more antisense oligonucleotides being from about 8 to about 30 nucleotides in length, targeted to a nucleic acid encoding either a wildtype or mutant human ras sequence which are capable, either individually or collectively, of modulating ras expression and (b) one or more chemotherapeutic compounds which do not function by an antisense mechanism.

An additional object of the invention is to provide liposome-based pharmaceutical compositions which inhibit the hyperproliferation of cells, including cancerous cells. Methods of inhibiting the hyperproliferation of cells, including cancerous cells, are also an object of this invention.

A further object of this invention is to provide methods of treatment of, and liposome-based pharmaceutical compositions for, conditions arising due to mutation of the gene from the wildtype to a mutant, activated form of the ras gene.

SUMMARY OF THE INVENTION

In accordance with the present invention sterically stabilized liposomes containing one or more antisense oligonucleotides and pharmaceutical compositions comprising such liposomes are provided, wherein the antisense oligonucleotides contained within the sterically stabilized liposomes are from about 8 to about 30 nucleotides in length, are targeted to a nucleic acid encoding a human ras sequence and are capable, either individually or collectively, of modulating ras expression.

Also provided are sterically stabilized liposomes containing one or more antisense oligonucleotides, and pharmaceutical compositions comprising such liposomes, wherein the antisense oligonucleotides contained within the sterically stabilized liposomes are from about 8 to about 30 nucleotides in length, are targeted to a nucleic acid encoding an activated (mutant) human ras sequence and are capable, either individually or collectively, of modulating the expression of the activated form of the ras gene.

Further provided are sterically stabilized liposomes containing (a) one or more antisense oligonucleotides being from about 8 to about 30 nucleotides in length, targeted to a nucleic acid encoding either a wildtype or mutant human ras sequence which are capable, either individually or collectively, of modulating ras expression and (b) one or more chemotherapeutic compounds which do not function by an antisense mechanism.

Liposome-based pharmaceutical compositions which inhibit the hyperproliferation of cells, including cancerous cells, are provided. Methods of inhibiting the hyperproliferation of cells, including cancerous cells, are also provided.

Methods of treatment of, and liposome-based pharmaceutical compositions for, conditions arising due to mutation of the gene from the wildtype to a mutant, activated form of the ras gene are also provided herein.

DETAILED DESCRIPTION OF THE INVENTION

Figure 1:
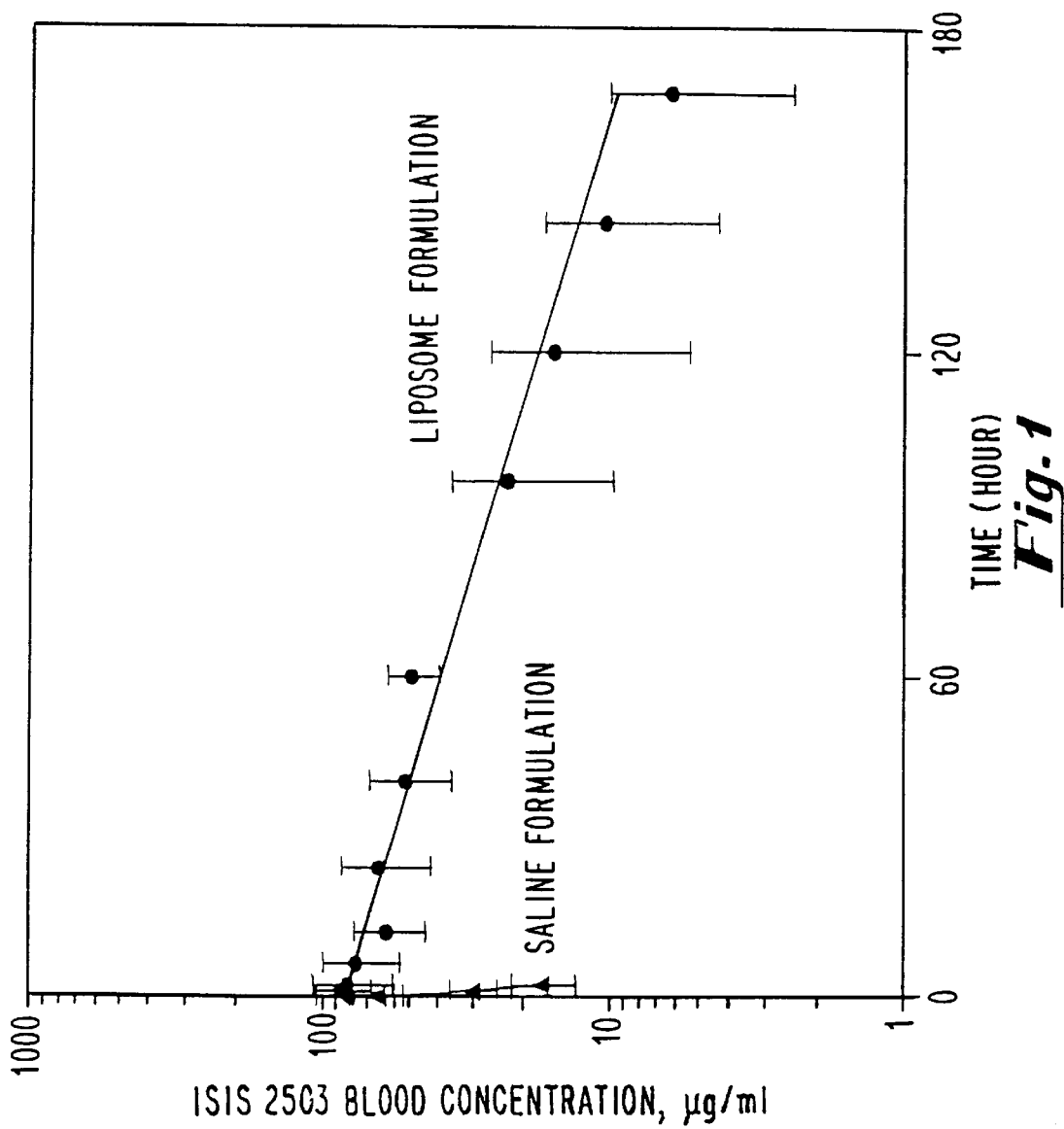
FIG. 1 shows the time course of the clearance of ISIS 2503 and oligonucleotide metabolites from blood. Each point is represented as the mean (symbol) ± standard deviation (n=1–8). Nonlinear regression was performed using a one compartment model (solid line). Symbols: ●, observed blood concentration for liposomal oligonucleotide formulation; the solid line indicates the predicted blood concentration for liposomal oligonucleotide formulation; ▲, observed blood concentration for saline formulation of ISIS 2503.
Figure 2:
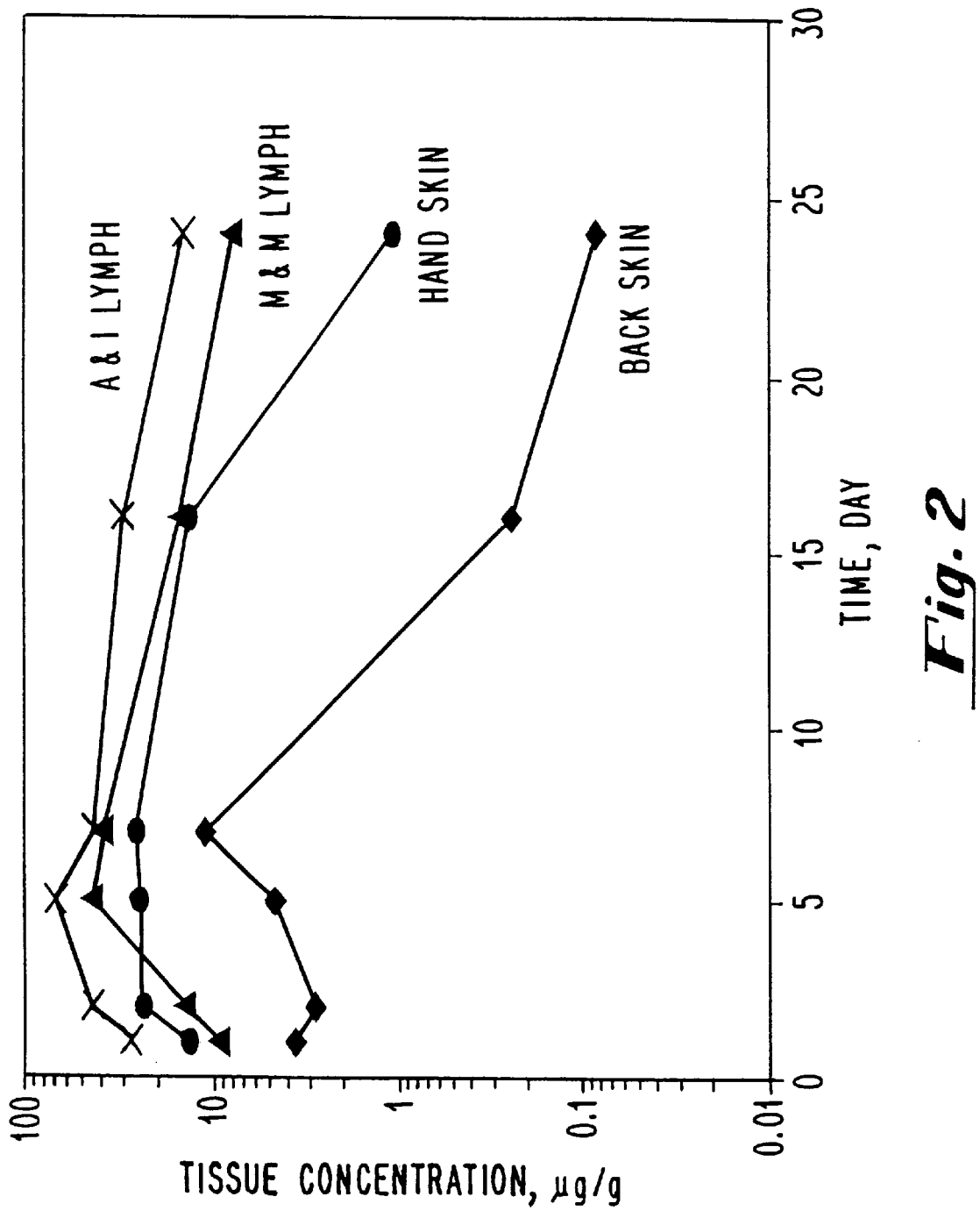
FIG. 2 shows the distribution and kinetics of full-length ISIS 2503 in monkey tissues at time points following a single 10 mg/kg intravenous infusion of ISIS 2503 encapsulated in sterically stabilized liposomes in the indicated tissues ("A & I Lymph"=axillary and inguinal lymph nodes, combined; "M & M Lymph"=mesenteric and mandibular lymph nodes, combined). Symbols: X, axillary and inguinal lymph nodes, combined; ▲, mesenteric and mandibular lymph nodes, combined; ●, hand skin; ♦, back skin.
Figure 3:
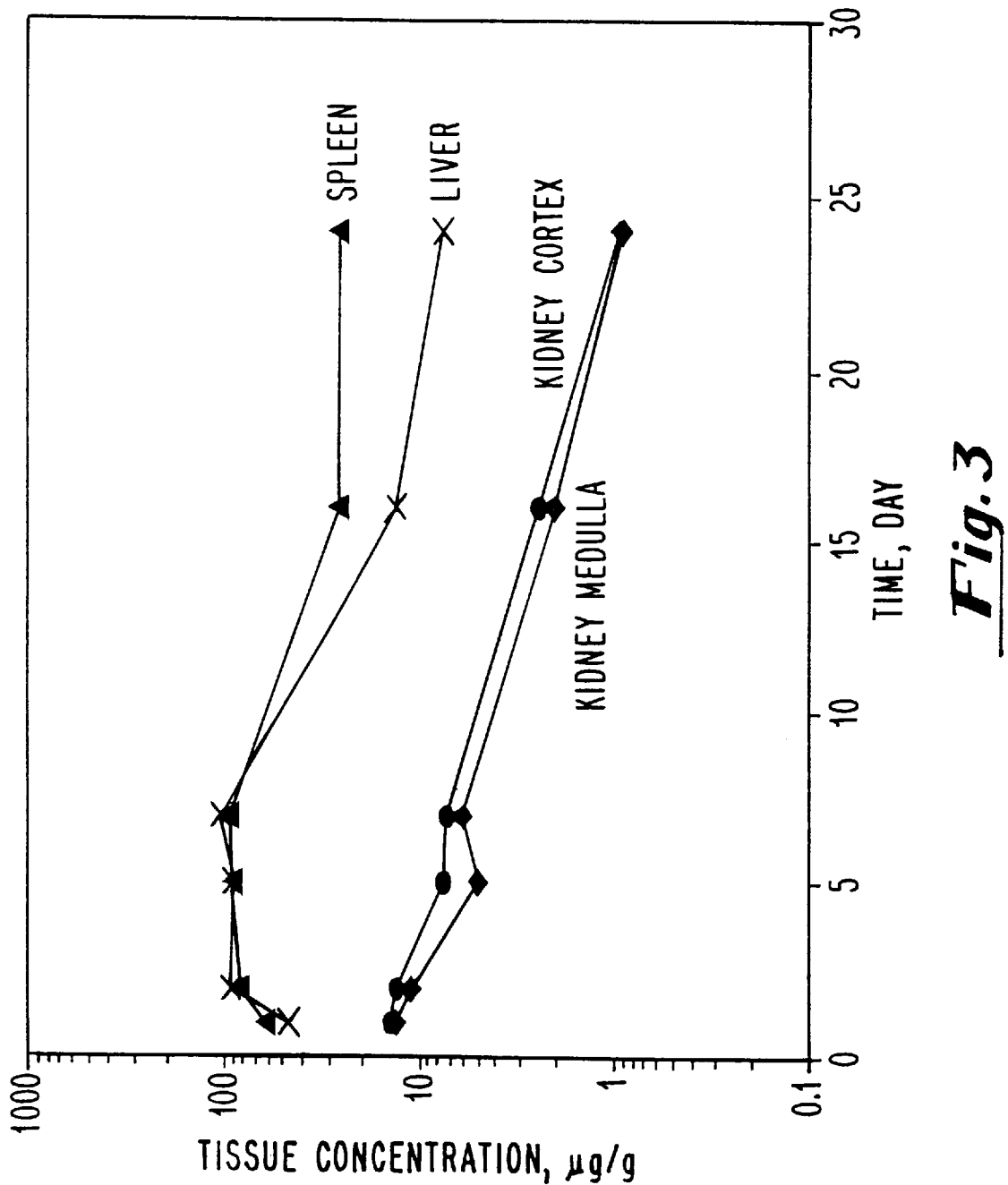
FIG. 3 shows the distribution and kinetics of full-length ISIS 2503 in monkey tissues at time points following a single 10 mg/kg intravenous infusion of ISIS 2503 encapsulated in sterically stabilized liposomes in the indicated tissues ("A & I Lymph"=axillary and inguinal lymph nodes, combined; "M & M Lymph"=mesenteric and mandibular lymph nodes, combined). Symbols: X, liver; ▲, spleen; ●, kidney cortex; ♦, kidney medulla.
Figure 4:
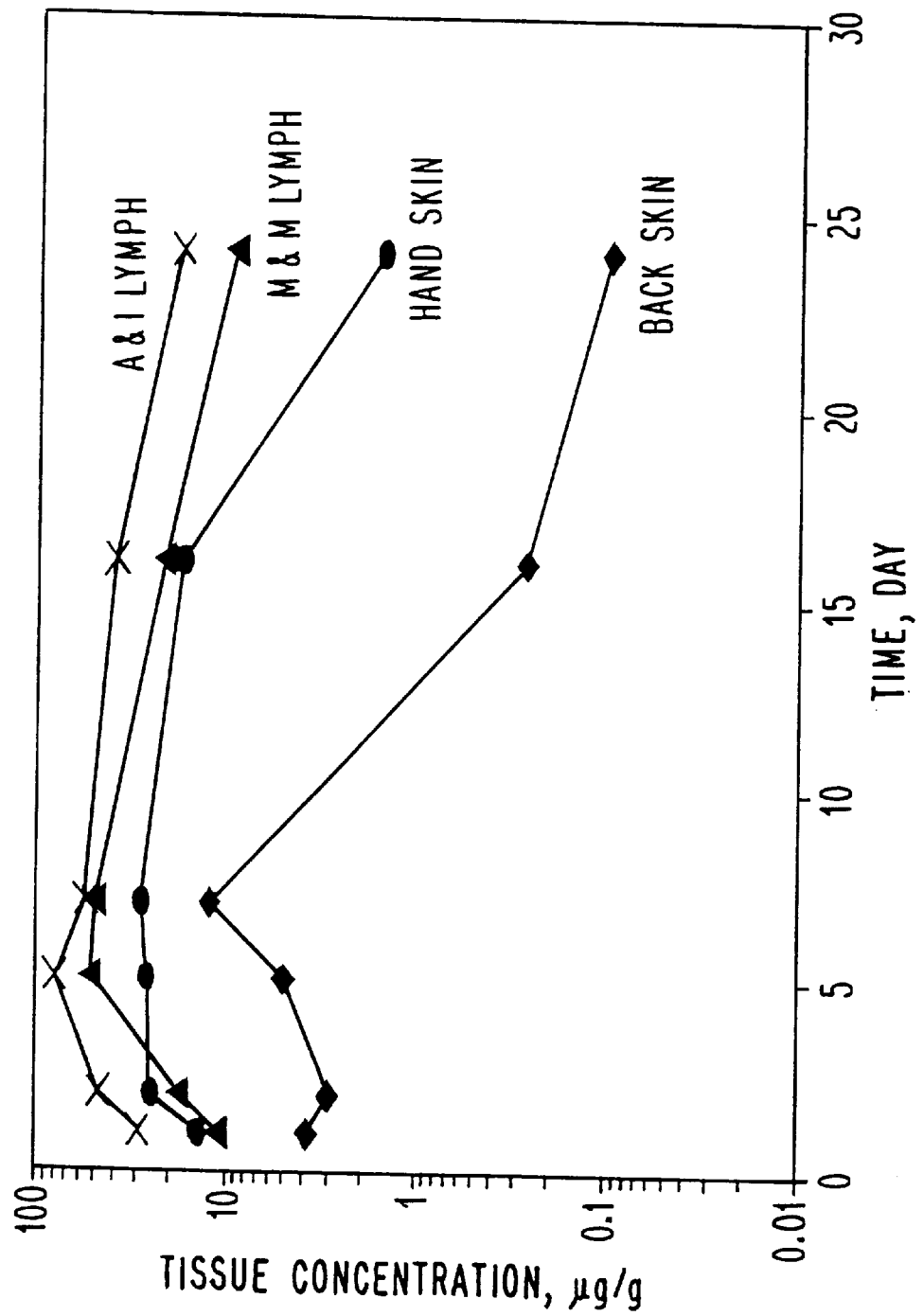
FIG. 4 shows the distribution and kinetics of total oligonucleotide in monkey tissues at time points following a single 10 mg/kg intravenous infusion of ISIS 2503 encapsulated in sterically stabilized liposomes in the indicated tissues ("A & I Lymph"=axillary and inguinal lymph nodes, combined; "M & M Lymph"=mesenteric and mandibular lymph nodes, combined). Symbols: X, axillary and inguinal lymph nodes, combined; ▲, mesenteric and mandibular lymph nodes, combined; ●, hand skin; ♦, back skin.
Figure 5:
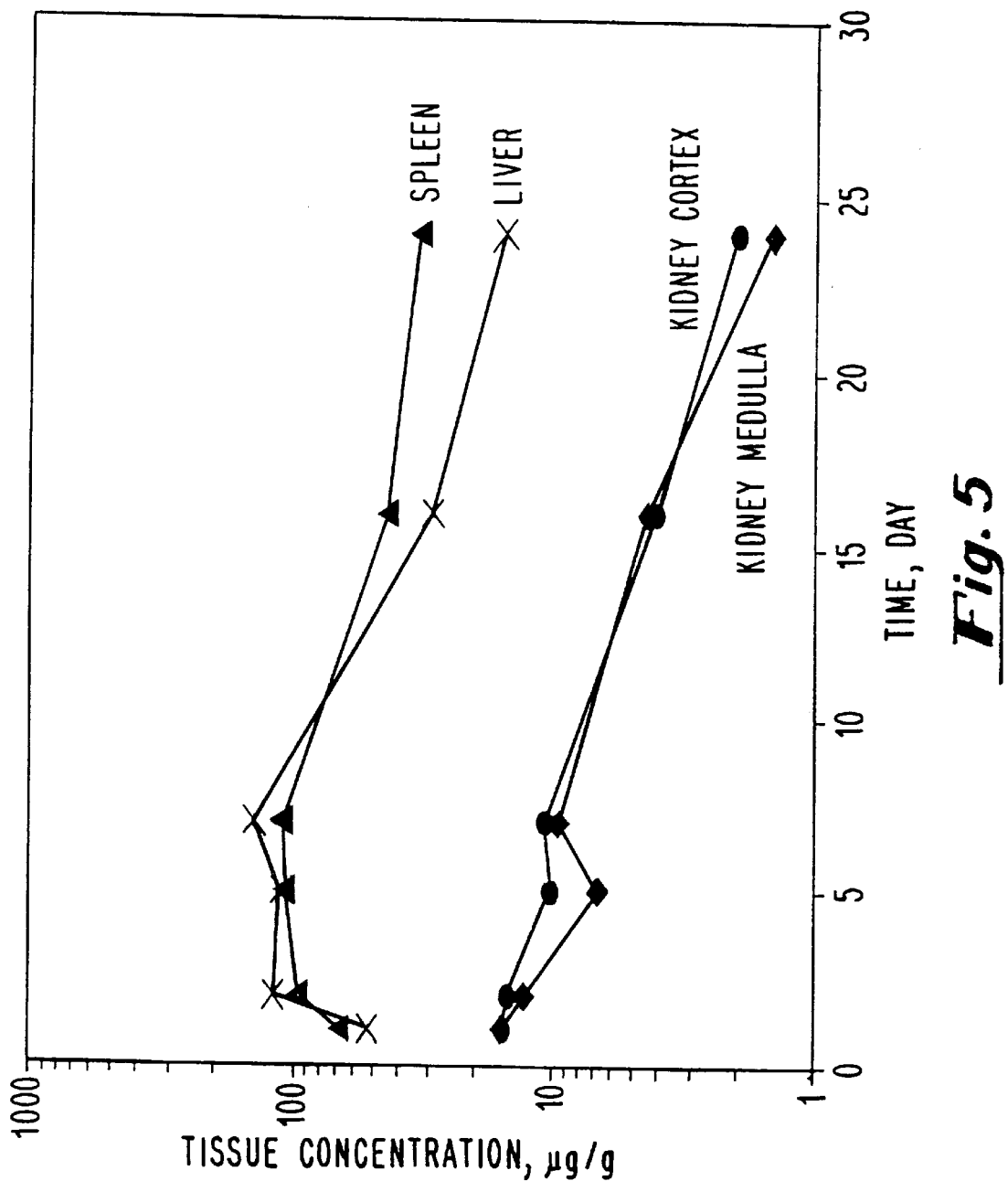
FIG. 5 shows the distribution and kinetics of total oligonucleotide in monkey tissues at time points following a single 10 mg/kg intravenous infusion of ISIS 2503 encapsulated in sterically stabilized liposomes in the indicated tissues ("A & I Lymph"=axillary and inguinal lymph nodes, combined; "M & M Lymph"=mesenteric and mandibular lymph nodes, combined). Symbols: X, liver; ▲, spleen; ●, kidney cortex; ♦, kidney medulla.

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. In addition, the ability to study cell transformation in carefully controlled, quantitative in vitro assays has led to the identification of specific genes capable of inducing the transformed cell phenotype. Such cancer-associated genes are believed to acquire transformation-inducing properties through mutations leading to changes in the regulation of expression of their protein products. In some cases such changes occur in non-coding DNA regulatory domains, such as promoters and enhancers, leading to alterations in the transcriptional activity of cancer associated genes, resulting in over- or under-expression of their gene products. In other cases, gene mutations occur within the coding regions of cancer associated genes, leading to the production of altered gene products that are inactive, overactive, or exhibit an activity that is different from the normal (wild-type) gene product.

Many cellular cancer associated gene families have been identified and categorized on the basis of their subcellular location and the putative mechanism of action of their protein products. The ras genes are members of a gene family which encode related proteins that are localized to the inner face of the plasma membrane. Ras proteins have been shown to be highly conserved at the amino acid level, to bind GTP with high affinity and specificity, and to possess GTPase activity (for a review, see Downward, *Trends Biochem. Sci.* 15:469, 1990). Although their cellular function(s) is(are) unknown, the biochemical properties of the ras proteins, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes. The ras gene product, $p21^{ras}$, interacts with a variety of known and proposed cellular effectors (for a review, see Marshall, *Trends Biochem. Sci.* 18:250, 1993)

Three ras genes, designated H-ras, K-ras, and N-ras, have been identified in the mammalian genome. Mammalian ras genes acquire transformation-inducing properties by single point mutations within their coding sequences. Mutations in naturally occurring ras genes have been localized to codons 12, 13, and 61. The sequences of H-ras, K-ras and N-ras are known (Capon et al., *Nature* 302:33, 1983; Kahn et al., *Anticancer Res.* 7:639, 1987; Hall and Brown, *Nucleic Acids Res.* 13:5255, 1985). The most commonly detected activating ras mutation found in human tumors is in codon 12 of the H-ras gene in which a base change from GGC to GTC results in a glycine-to-valine substitution in the GTPase regulatory domain of the ras protein product (Tabin et al., *Nature*, 300:143, 1982; Reddy et al., *Nature* 300:149, 1982; Taparowsky et al., *Nature* 300:762, 1982). This single amino acid change is thought to abolish normal control and/or function of $p21^{H-ras}$, thereby converting a normally regulated cell protein to one that is continuously active. It is believed that such deregulation of normal ras protein function is responsible for the transformation from normal to malignant growth.

The present invention provides pharmaceutical compositions comprising sterically stabilized liposomes containing one or more antisense oligonucleotides, wherein the antisense oligonucleotides contained within the sterically stabilized liposomes are from about 8 to about 30 nucleotides in length, more preferably from about 8 to about 30 nucleotides in length, are targeted to a nucleic acid encoding a human wildtype or mutant ras sequence and are capable, individually and/or collectively, of modulating ras expression. In another embodiment, the sterically stabilized liposomes of the invention contain (a) one or more such antisense oligonucleotides and (b) one or more chemotherapeutic compounds which do not function by an antisense mechanism. The remainder of the Detailed Description relates in more detail to (1) the oligonucleotides of the invention, (2) their bioequivalents, (3) sterically stabilized liposomes, (4) chemotherapeutic agents that can be combined with antisense oligonucleotides targeted to H-ras in the context of the liposomes of the invention and (5) administration of pharmaceutical compositions comprising the liposomal oligonucleotide compositions of the invention.

1. Oligonucleotides: In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of a repeating unit generically known as a nucleotide. The oligonucleotides in accordance with this invention preferably comprise from about 8 to about 30 nucleotides. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'–5' phosphate linkage. The "backbone" of an unmodified oligonucleotide consists of (2) and (3), that is, sugars linked together by phosphodiester linkages between the 5' carbon of the sugar of a first nucleotide and the 3' carbon of a second, adjacent nucleotide. A "nucleoside" is the combination of (1) a nucleobase and (2) a sugar in the absence of (3) a phosphate moiety (Kornberg, A., *DNA Replication*, W. H. Freeman & Co., San Francisco, 1980, pages 4–7). The backbone of an oligonucleotide positions a series of bases in a specific order; the written representation of this series of bases, which is conventionally written in 5' to 3' order, is known as a nucleotide sequence.

The oligonucleotides used in accordance with this invention may be conveniently and routinely made through the well-known technique of solid phase synthesis. Equipment for such synthesis is sold by several vendors including Applied Biosystems (Foster City, Calif.). Any other means for such synthesis may also be employed, however, the actual synthesis of the oligonucleotides are well within the talents of the routineer. It is also well known to use similar techniques to prepare other oligonucleotides such as the phosphorothioates and alkylated derivatives.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine, 5-hydroxymethylcytosine (HMC), glycosyl HMC and gentiobiosyl HMC (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by any chemical modification to a nucleobase in the nucleotide sequence of the oligonucleotide which does not significantly effect its specificity for the partner nucleobase in the target oligonucleotide. It is understood in the art that an oligonucleotide need not be 100% complementary to its target DNA sequence to be specifically hybridizable. An oligonucleotide is specifically hybridizable when there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed. The nucleotide sequences of the oligonucleotides of the invention are given in Example 1 and also in the Sequence Listing. Citations for target H-ras sequences are also presented in Example 1.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses.

A. Modified Linkages: Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254:1497; U.S. Pat. No. 5,539,082).

B. Modified Nucleobases: The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine (Kornberg, A., *DNA Replication*, W. H. Freeman & Co., San Francisco, 1980, pages 75–77; Gebeyehu, G., et al., *Nucleic Acids Res.*, 1987, 15, 4513).

C. Sugar Modifications: The oligonucleotides of the invention may additionally or alternatively comprise substitutions of the sugar portion of the individual nucleotides. For example, oligonucleotides may also have sugar mimetics such as cyclobutyls in place of the pentofuranosyl group. Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O—(2-methoxyethyl)] (Martin et al., *Helv. Chim. Acta*, 1995, 78:486). Other preferred modifications include 2'-methoxy-(2'-O—$CH_3$), 2'-propoxy-(2'-$OCH_2CH_2CH_3$) and 2'-fluoro-(2'—F).

D. Other Modifications: Similar modifications may also be made at other positions on the oligonucleotide, particularly the 3' position of the sugar on the 3' terminal nucleotide and the 5' position of 5' terminal nucleotide. The 5' and 3' termini of an oligonucleotide may also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology, Volume* 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., *Nucleic Acids Res.*, 1987, 15:4513). Such lipophilic moieties include but are not limited to a cholesteryl moiety (Letsinger et al., *Proc. Natl. Acad. Sci. U.S.A.*, 1989, 86:6553), cholic acid (Manoharan et al., *Bioorg. Med. Chem. Let.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylaminocarbonyl-oxycholesterol moiety (Crooke et al., *J. Pharmacol. Exp. Ther.*, 1996, 277:923). Oligonucleotides comprising lipophilic moieties, and methods for preparing such oligonucleotides, are disclosed in co-owned U.S. Pat. Nos. 5,138,045, 5,218,105 and 5,459,255.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (see co-owned U.S. Pat. No. 5,587,361 to Cook et al.) and those having substantially chirally pure (Sp or Rp) alkylphosphonate, phosphoamidate or phosphotriester linkages (see co-owned U.S. Pat. Nos. 5,212,295 and 5,521,302).

E. Chimeric Oligonucleotides: The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy-substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy-substituted), or vice-versa.

F. Synthesis: The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

1. Teachings regarding the synthesis of particular modified oligonucleotides may be found in the following U.S. patents or pending patent applications, each of which is commonly assigned with this application and is hereby incorporated by reference: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having b-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides. In 2'-methoxyethoxy-modified oligonucleotides, 5-methyl-2'-methoxyethoxy-cytosine residues are used and prepared as described in pending application Ser. No. 08/731,199, filed Oct. 4, 1996. Specific methods for preparing MMI linkages are taught in U.S. Pat. Nos. 5,378,825 (issued Jan. 3, 1995), 5,386,023 (issued Jan. 31, 1995), 5,489,243 (issued on Feb. 6, 1996), 5,541,307 (issued on Jul. 30, 1996), 5,618,704 (issued Apr. 8, 1997) and 5,623,070 (issued Apr. 22, 1997). MMI is an abbreviation for methylene(methylimino) that in turn is a shorten version of the more complex chemical nomenclature "3'-de(oxyphophinico)-3'[methylene(methylimino)]." Irrespective of chemical nomenclature, the linkages are as described in these patents. The linkages of these patents have also been described in various scientific publications by the inventors and their co-authors including Bhat et al. (*J. Org. Chem.* 61:8186, 1996, and references cited therein).

2. Bioequivalents: The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the oligonucleotides of the invention, pharmaceutically acceptable salts of such prodrugs, and other bioequivalents.

A. Oligonucleotide Prodrugs: The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec.9, 1993.

B. Pharmaceutically Acceptable Salts: The term "pharmaceutically acceptable salts" refers to physiologically and pharmaceutically acceptable salts of the oligonucleotides of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation including, for example, alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

3. Sterically Stabilized Liposomes: In compositions of the invention, one or more antisense oligonucleotides and/or therapeutic agents are entrapped within sterically stabilized liposomes. Liposomes are microscopic spheres having an aqueous core surrounded by one or more outer layer(s) made up of lipids arranged in a bilayer configuration (see, generally, Chonn et al., *Current Op. Biotech.* 6:698, 1995). The therapeutic potential of liposomes as drug delivery agents was recognized nearly thirty years ago (Sessa et al., *J. Lipid Res.* 9:310, 1968). Liposomes include "sterically stabilized liposome," a term which, as used herein, refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters* 223:42, 1987; Wu et al., *Cancer Research* 53:3765, 1993).

A. Glycolipid-comprising liposomes: Various liposomes comprising one or more glycolipids are known in the art. Papahadjopoulos et al. (*Ann. N.Y. Acad. Sci.*, 507:64, 1987) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.* 85:6949, 1988). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

B. Liposomes derivatized with hydrophilic polymers: Many liposomes comprising lipids derivatized with one or more hydrophilic polymers, and methods of preparation thereof, are known in the art. Sunamoto et al. (*Bull. Chem. Soc. Jpn.* 53:2778, 1980) described liposomes comprising a nonionic detergent, $2C_{12}15G$, that contains a PEG moiety. Illum et al. (*FEBS Letters* 167:79, 1984) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Letts.* 268:235, 1990) described experiments demonstrating that liposomes comprising phosphatidylethanolamine (PE) derivatized with PEG or PEG stearate have significant increases in blood circulation half-lives. Plume et al. (*Biochimica et Biophysica Acta* 1029:91, 1990) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

C. Liposomes comprising nucleic acids: A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses proteinbonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene. 4. Chemotherapeutic Agents: Certain embodiments of the invention provide for sterically stabilized liposomes containing (a) one or more antisense oligonucleotides targeted to a nucleic acid encoding a ras protein and (b) one or more chemotherapeutic agents which do not function by an antisense mechanism. In a related embodiment, such chemotherapeutic agents are co-administered with one or more of the liposomal oligonucleotide compositions of the invention but are separately encapsulated in distinct liposomes or are administered by a non-liposomal delivery mechanism. As used herein, a "chemotherapeutic agent" is an anticancer agents that functions via a conventional (i.e., non-antisense) mode of action. Examples of such chemotherapeutic agents include, but are not limited to, daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahay, N.J., pages 1206–1228). When used with the liposomal oligonucleotide compositions of the invention, such chemotherapeutic agents may be used individually, sequentially (e.g., 5-FU for a period of time followed by MTX), or in combination with one or more other such chemotherapeutic agents (e.g., 5-FU and MTX).

In a related embodiment, sterically stabilized liposomes containing (a) one or more antisense oligonucleotides targeted to a first nucleic acid encoding a ras sequence and (b) one or more additional antisense oligonucleotides targeted to a second nucleic acid encoding a cancer associated gene. By the term "cancer associated gene" is intended any cellular or viral gene the expression of which disrupts regulation of the cell cycle, negatively effects contact inhibition of growth, leads to cellular hyperproliferation, promotes pre-metastatic or metastatic events and/or otherwise leads to cellular hyperproliferation, tumor formation and the growth and spread of cancers, regardless of mechanism of action. In a related embodiment, such additional antisense oligonucleotides targeted to a second cancer-associated gene are co-administered with one or more of the liposomal oligonucleotide compositions of the invention but are separately encapsulated in distinct liposomes or are administered by a non-liposomal delivery mechanism. Such antisense oligonucleotides targeted to a second cancer associated gene include, but are not limited to, those directed to the following targets as disclosed in the indicated co-owned U.S. Patents, pending applications or published PCT applications, which are hereby incorporated by reference: raf (WO 96/39415, WO 95/32987 and U.S. Pat. Nos. 5,563,255, issued Oct. 8, 1996, and 5,656,612, issued Aug. 12, 1997), the p120 nucleolar antigen (WO 93/17125 and U.S. Pat. No. 5,656,743, issued Aug. 12, 1997), protein kinase C (WO 95/02069, WO 95/03833 and WO 93/19203), multidrug resistance-associated protein (WO 95/10938 and U.S. Pat. No. 5,510,239, issued Mar. 23, 1996), subunits of transcription factor AP-1 (co-pending application U.S. Ser. No. 08/837,201, filed Apr. 14, 1997), Jun kinases (co-pending application U.S. Ser. No. 08/910,629, filed Aug. 13, 1997), and MDR-1 (multidrug resistance glycoprotein; co-pending application U.S. Ser. No. 08/731,199, filed Sep. 30, 1997).

5. Administration of Pharmaceutical Compositions: The formulation of pharmaceutical compositions comprising the liposomal oligonucleotide compositions of the invention and their subsequent administration is believed to be within the skill of those in the art. In general, for therapeutics, a patient in need of such therapy is administered a liposomal oligonucleotide composition in accordance with the invention, commonly in a pharmaceutically acceptable carrier, in doses ranging from 0.01 $\mu$g to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide being administered via a particular mode of administration. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics*, 9th Ed., Hardman et al., eds., McGraw-Hill, New York, N.Y., 1996).

In some cases it may be more effective to treat a patient with a liposomal oligonucleotide composition of the invention in conjunction with other, traditional therapeutic modalities in order to increase the efficacy of a treatment regimen. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the pharmaceutical composition may either be increased in the event the patient does not respond significantly to current dosage levels, or the dose may be decreased if an alleviation of the symptoms of the disorder or disease state is observed, or if the disorder or disease state has been ablated.

As used herein, the term "high risk individual" is meant to refer to an individual for whom it has been determined, via, e.g., individual or family history or genetic testing, that there is a significantly higher than normal probability of being susceptible to the onset or recurrence of a disease or disorder. As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

The pharmaceutical compositions of the present invention may be administered in a number of ways depending upon whether local or systemic treatment is desired and upon the area to be treated. Typically, parenteral administration is employed. The term "parenteral delivery" refers to the administration of an oligonucleotide of the invention to an animal in a manner other than through the digestive canal. Parenteral administration includes intravenous (i.v.) drip, subcutaneous, intraperitoneal (i.p.) or intramuscular injection, or intrathecal or intraventricular administration. Compositions for parenteral, intrathecal or intraventricular administration may include sterile aqueous solutions which may also contain buffers, diluents and other suitable additives. Means of preparing and administering parenteral pharmaceutical compositions are known in the art (see, e.g., Avis, Chapter 84 In: *Remington's Pharmaceutical Sciences*, 18th Ed., Gennaro, ed., Mack Publishing Co., Easton, Pa., 1990, pages 1545–1569). Parenteral means of delivery include, but are not limited to, the following illustrative examples.

(A) Intravitreal injection, for the direct delivery of drug to the vitreous humor of a mammalian eye, is described in U.S. Pat. No. 5,591,720, the contents of which are hereby incorporated by reference. Means of preparing and administering ophthalmic preparations are known in the art (see, e.g., Mullins et al., Chapter 86 In: *Remington's Pharmaceutical Sciences*, 18th Ed., Gennaro, ed., Mack Publishing Co., Easton, Pa., 1990, pages 1581–1595).

(B) Intravenous administration of antisense oligonucleotides to various non-human mammals has been described by Iversen (Chapter 26 In: *Antisense Research and Applications*, Crooke et al., eds., CRC Press, Boca Raton, Fla., 1993, pages 461–469). Systemic delivery of oligonucleotides to non-human mammals via intraperitoneal means has also been described (Dean et al., *Proc. Natl. Acad. Sci. U.S.A.* 91:11766, 1994).

(C) Intraluminal drug administration, for the direct delivery of drug to an isolated portion of a tubular organ or tissue (e.g., such as an artery, vein, ureter or urethra), may be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the oligonucleotides of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci. U.S.A.* 90:8474, 1993). Antisense oligonucleotides may also be combined with a biocompatible matrix, such as a hydrogel material, and applied directly to vascular tissue in vivo (Rosenberg et al., U.S. Pat. No. 5,593,974, issued Jan. 14, 1997).

(D) Intraventricular drug administration, for the direct delivery of drug to the brain of a patient, may be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research* 44:1698, 1984; Shaw, *Cancer* 72(11 Suppl.):, 3416, 1993). The pump is used to inject the oligonucleotides and allows precise *dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 µg to 100 g per kg of body weight, the pump reservoir may be refilled at 3–10 week intervals. Refilling of the pump is accomplished by percutaneous puncture of the pump's self-sealing septum.

(E) Intrathecal drug administration, for the introduction of a drug into the spinal column of a patient may be desired for the treatment of patients with diseases of the central nervous system (CNS). To effect this route of oligonucleotide administration, a silicon catheter is surgically implanted into the L3-4 lumbar spinal interspace of a human patient, and is connected to a subcutaneous infusion pump which has been surgically implanted in the upper abdominal region (Luer and Hatton, *The Annals of Pharmacotherapy* 27:912, 1993; Ettinger et al. Cancer, 41:1270, 1978; Yaida et al., *Regul. Pept.* 59:193, 1985). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 µg to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the CNS are followed according to known methods (Whitesell et al., *Proc. Natl. Acad. Sci. U.S.A.* 90:4665, 1993).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer* 71:1964, 1993). Infusion pumps may also be used to effect systemic delivery of oligonucleotides (Ewel et al., *Cancer Research* 52:3005, 1992; Rubenstein et al., *J. Surg. Oncol.* 62:194, 1996).

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Nucleic Acid Sequences

The oligonucleotides of this invention are designed to be complementary to, and thus hybridizable with, messenger RNA derived from a ras gene. Such hybridization, when accomplished, interferes with the normal roles of the messenger RNA to cause a loss of its function in the cell. The functions of messenger RNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to interfere with expression of the ras gene. Some oligonucleotides of this invention are designed to activate RNAse H cleavage of the ras mRNA.

The protein products of the other mammalian ras genes, N-ras and K-ras, are identical to H-ras over the first 85 amino acids. However, the nucleic acid sequences of the three ras genes are not identical, and persons of ordinary skill in the art will be able to use this invention as a guide in preparing oligonucleotides specifically hybridizable with a particular ras gene. While one preferred embodiment of the invention relate to antisense oligonucleotides specifically hybridizable with codon 12 of the H-ras mRNA, the disclosure can be used by persons skilled in the art as a guide in preparing oligonucleotides specifically hybridizable with other point mutations of the H-ras gene, particularly the well defined point mutations at codon 12, codon 13 and codon 61 of H-ras, or point mutations within other ras genes.

The nucleotide sequence of wildtype (wt) H-ras, also known as Ha-ras, has been described by Capon et al. (*Nature* 302:33, 1983), Fasano et al. (*J. Mol. Appl. Genet.* 2:173, 1983), Reddy (*Science* 220:1061, 1983) and Honkawa et al. (*Mol. Cell. Biol.* 7:2933, 1987). Mutant (activated) H-ras sequences have been reported by Tabin et al. (*Nature* 300:143, 1982), Taparowsky et al. (*Nature* 300:762, 1982), Yuasa et al. (*Nature* 303:775, 1983), Sekiya et al. (*Proc. Natl. Acad. Sci. USA* 81:4771, 1984; *Jpn. J. Cancer Res.* 76:787, 1985), Kraus et al. (*Proc. Natl. Acad. Sci. USA* 81:5384, 1984), Stevens et al. (*Proc. Natl. Acad. Sci. USA* 85:3875), Deng et al. (*Cancer Res.* 47:3195, 1987), Santos et al. (*Proc. Natl. Acad. Sci. USA* 80:4679, 1983), Tanci et al. (*Nucleic Acids Res.* 20:1157, 1992) and Tadokoro et al. (*Oncogene* 4:499, 1989). The sequences of wildtype and mutant H-ras genes may also be found in the Genbank and EMBOL databases under Accession Nos. J00206, J00276, J00277, K00654, K00954, M30539, M19990, M17232, M25876, V00574, X01227 and X16438.

The nucleotide sequence of wildtype (wt) K-ras, also known as Ki-ras, has been described by McGrath et al. (*Nature* 304:501, 1983) and McCoy et al. (*Mol. Cell. Biol.* 4:1577, 1984). Mutant (activated) K-ras sequences have been reported by Shimizu et al. (*Nature* 304:497, 1983), Capon et al. (*Nature* 304:507, 1983), Nakano et al. (*Proc. Natl. Acad. Sci. U.S.A.* 81:71, 1984), Taya et al. (*EMBO J.* 3:2943, 1984) and Nardeux et al. (*Biochem. Biophys. Res. Commun.* 146:395, 1987). The sequences of wildtype and mutant K-ras genes may also be found in Genbank under Accession Nos. K00652, K00653, K01519, K01520, K01912, L00045, L00049, M17087, M26261, M38506 and M54968.

The nucleotide sequences of wildtype and mutant N-ras genes are known (Hall et al., *Nucleic Acids Res.* 13:5255, 1985; Taparowsky et al., *Cell* 34:581, 1983; Geis et al., *Biochem. Biophys. Res. Commun.* 139:771, 1986; Brown et al., *EMBO J.* 3:1321, 1984). The sequences of wildtype and mutant N-ras genes may also be found in the Genbank and EMBOL databases under Accession Nos. K00082, L00043, M14307, X00645 and X02751.

Oligonucleotides targeted to ras genes are described in U.S. Pat. Nos. 5,576,208; 5,582,972; 5,582,986; and 5,661,134, and pending application Ser. No. 08/889,296, filed Jul. 8, 1997, as well as WO 94/08003, WO 94/28720 and WO 92/22651 to Monia et al., all of which are assigned to the same assignee as that of the present disclosure and which are hereby incorporated by reference.

The sequences and chemistries of oligonucleotides targeted to H-ras are detailed in Tables 1 through 7. The sequences and chemistries of oligonucleotides targeted to K-ras are detailed in Table 8. Sequences and chemistries of oligonucleotides targeted to N-ras are detailed in Table 9.

TABLE 1

Phosphorothioate Antisense Oligodeoxynucleotides Targeted to H-ras

*Targeted to the H-ras translation initiation codon*

| ISIS # | SEQUENCE (5'->3') | SEQ ID NO: |
|---|---|---|
| 2502 | CTT-ATA-TTC-CGT-CAT-CGC-TC | 1 |
| 2503 | TCC-GTC-ATC-GCT-CCT-CAG-GG | 2 |
| 2570 | CCA-CAC-CGA-CGG-CGC-CC | 3 |
| 2571 | CCC-ACA-CCG-ACG-GCG-CCC-A | 4 |
| 2566 | GCC-CAC-ACC-GAC-GGC-GCC-CAC | 5 |
| 2560 | TGC-CCA-CAC-CGA-CGG-CGC-CCA-CC | 6 |

*Targeted to mutant H-ras*

| ISIS # | TARGET | SEQUENCE (5'->3') | SEQ ID NO: |
|---|---|---|---|
| 2502 | AUG | CTTATATTCCGTCATCGCTC | 1 |
| 2503 | AUG | TCCGTCATCGCTCCTCAGGG | 2 |
| 6186 | AUG | TATTCCGTCATCGCTCCTCA | 7 |
| 2563 | CODON 12 | CGACG | 8 |
| 2564 | CODON 12 | CCGACGG | 9 |
| 2565 | CODON 12 | ACCGACGGC | 10 |
| 2567 | CODON 12 | CACCGACGGCG | 11 |
| 2568 | CODON 12 | ACACCGACGGCGC | 12 |
| 2569 | CODON 12 | CACACCGACGGCGCC | 13 |

TABLE 1-continued

Phosphorothioate Antisense Oligodeoxynucleotides Targeted to H-ras

| ISIS # | | SEQUENCE | SEQ ID NO: |
|---|---|---|---|
| 3426 | CODON 12 | CCACACCGACGGCGCC | 14 |
| 3427 | CODON 12 | CACACCGACGGCGCCC | 15 |
| 2570 | CODON 12 | CCACACCGACGGCGCCC | 3 |
| 3428 | CODON 12 | CCCACACCGACGGCGCCC | 16 |
| 3429 | CODON 12 | CCACACCGACGGCGCCCA | 17 |
| 2571 | CODON 12 | CCCACACCGACGGCGCCCA | 4 |
| 2566 | CODON 12 | GCCCACACCGACGGCGCCCAC | 5 |
| 2560 | CODON 12 | TGCCCACACCGACGGCGCCCACC | 6 |
| 2561 | CODON 12 | TTGCCCACACCGACGGCGCCCACCA | 18 |
| 2907 | CODON 12 (wt) | CCACACCGCCGGCGCCC | 19 |

TABLE 2

Chimeric Phosphorothioate Oligonucleotides Having 2'-O-Methyl Ends (Bold) and Central Deoxy Gap
(Mutant Codon-12 Target)

| ISIS # | # OF DEOXY RESIDUES | SEQUENCE (5'->3') | SEQ ID NO: |
|---|---|---|---|
| 4122 | 0 | CCACACCGACGGCGCCC | 3 |
| 3975 | 1 | CCACACCGACGGCGCCC | 3 |
| 3979 | 3 | CCACACCGACGGCGCCC | 3 |
| 4236 | 4 | CCACACCGACGGCGCCC | 3 |
| 4242 | 4 | CCACACCGACGGCGCCC | 3 |
| 3980 | 5 | CCACACCGACGGCGCCC | 3 |
| 3985 | 7 | CCACACCGACGGCGCCC | 3 |
| 3984 | 9 | CCACACCGACGGCGCCC | 3 |
| 2570 | 17 | CCACACCGACGGCGCCC | 3 |

TABLE 3

Shortened Phosphorothioate Chimeric Oligonucleotides Derived from ISIS 3980 Having 2'-O-Methyl Ends (Bold) and Central Deoxy Gap
(Mutant Codon-12 Target)

| ISIS # | SEQUENCE (5'->3') | SEQ ID NO: |
|---|---|---|
| 3980 | CCACACCGACGGCGCCC | 3 |
| 4230 | CACACCGACGGCGCC | 13 |
| 4276 | ACACCGACGGCGC | 12 |
| 4247 | CACCGACGGCG | 11 |

TABLE 3-continued

Shortened Phosphorothioate Chimeric Oligonucleotides Derived from ISIS 3980 Having 2'-O-Methyl Ends (Bold) and Central Deoxy Gap
(Mutant Codon-12 Target)

| ISIS # | SEQUENCE (5'->3') | SEQ ID NO: |
|---|---|---|
| 3985 | CCACACCGACGGCGCCC | 3 |
| 4245 | CACACCGACGGCGCC | 13 |
| 4278 | ACACCGACGGCGC | 12 |
| 4229 | CACCGACGGCG | 11 |

TABLE 4

Chimeric Phosphorothioate Oligonucleotides Having 2'-O-Methyl Ends (Bold) and Central Deoxy Gap
(AUG Target)

| ISIS # | # OF DEOXY RESIDUES | SEQUENCE (5'->3') | SEQ ID NO: |
|---|---|---|---|
| 2502 | 20 | CTTATATTCCGTCATCGCTC | 1 |
| 4998 | 7 | CTTATATTCCGTCATCGCTC | 1 |
| 2503 | 20 | TCCGTCATCGCTCCTCAGGG | 2 |
| 5122 | 7 | TCCGTCATCGCTCCTCAGGG | 2 |

TABLE 5

Chimeric Backbone (P = S/P = O) Oligonucleotides
Having 2'-O-Methyl Ends (Bold) and Central Deoxy Gap
(Backbone Linkages Indicated by "s" (P = S) or "o" (P = O)
(Mutant Codon-12 Target)

| ISIS # | # OF DEOXY RESIDUES | SEQUENCE (5'->3') | SEQ ID NO: |
|---|---|---|---|
| 2570 | 16 | CsCsAsCsAsCsCsGsAsCsGsGsCsGsCsCsC | 3 |
| 4226 | 5 | CoCoAoCoAoCsCsGsAsCsGoGoCoGoCoCoC | 3 |
| 4233 | 11 | CsCsAsCsAsCoCoGoAoCoGsGsCsGsCsCsC | 3 |
| 4248 | 15 | CsCsAsCsAsCsCsGsAoCsGsGsCsGsCsCsC | 3 |
| 4546 | 14 | CsCsAsCsAsCsCsGoAoCsGsGsCsGsCsCsC | 3 |
| 4551 | 13 | CsCsAsCsAsCsCsGoAoCsGoGsCsGsCsCsC | 3 |
| 4593 | 12 | CsCsAsCsAsCsCoGoAoCoGsGsCsGsCsCsC | 3 |
| 4606 | 11 | CsCsAsCsAsCsCoGoAoCoGoGsCsGsCsCsC | 3 |
| 4241 | 6 | CsCsAsCoAoCoCoGoAoCoGoGoCoGsCsCsC | 3 |

TABLE 6

Phosphorothioate Antisense Oligodeoxynucleotides
Targeted to a Hairpin Structure Corresponding
to Residues +18 to +64 of the Coding Sequence
of Activated H-ras mRNA

| ISIS # | SEQUENCE (5'->3') | SEQ ID NO: |
|---|---|---|
| 3270 | CACCACCACC | 20 |
| 3271 | GCGCCCACCA | 21 |
| 3292 | CGACGGCGCC | 22 |
| 3291 | CACACCGACG | 23 |
| 3283 | UUGCCCACAC | 24 |
| 3284 | CACUCUUGCC | 25 |

TABLE 7

2'-Modified Analogs of ISIS 2503
(Positions with 2' Modifications are Emboldened)

*MOE Analogs (positions with 2'-MOE are emboldened)*

| ISIS # | Sequence (5'->3') | SEQ ID NO: |
|---|---|---|
| 13905 | TCCGTCATCGCTCCTCAGGG | 2 |
| 13907 | TCCGTCATCGCTCCTCAGGG | 2 |
| 13909 | TCCGTCATCGCTCCTCAGGG | 2 |
| 13911 | TCCGTCATCGCTCCTCAGGG | 2 |
| 13917 | TCCGTCATCGCTCCTCAGGG | 2 |
| 13919 | TCCGTCATCGCTCCTCAGGG | 2 |
| 13920 | TCCGTCATCGCTCCTCAGGG | 2 |

TABLE 7-continued

2'-Modified Analogs of ISIS 2503
(Positions with 2' Modifications are Emboldened)

| ISIS # | Sequence | SEQ ID NO: |
|---|---|---|
| 13923 | TCCGTCATCGCTCCTCAGGG | 2 |
| 13926 | TCCGTCATCGCTCCTCAGGG | 2 |
| 13927 | TCCGTCATCGCTCCTCAGGG | 2 |

*MMI Analogs (positions with 2'-MOE are emboldened)*

| ISIS # | Sequence (5'->3') | SEQ ID NO: |
|---|---|---|
| 14896 | TCCGTCATCGCTCCTCAGGG | 2 |
| 14897 | TCoCGTCATCGCTCCTCAGoGG | 2 |
| 14898 | TCsCGTCATCGCTCCTCAGsGG | 2 |
| 14899 | TCoCGoTCATCGCTCCoTCoAoGGG | 2 |
| 14900 | TCsCGsTCATCGCTCCsTCsAGsAG | 2 |

"o" indicates a phosphodiester linkage between MMI dimers;
"s" indicates a phosphorothioate linkage between MMI dimers.
All unmarked linkages are phosphorothioates.

TABLE 8

Phosphorothioate Antisense Oligonucleotides Targeted to Human K-ras

*Oligodeoxynucleotides*

| ISIS # | SEQUENCE (5'->3') | TARGET | SEQ ID NO: |
|---|---|---|---|
| 6958 | CTGCCTCCGCCGCCGCGGCC | 5' UTR/5'-cap | 28 |
| 6957 | CAGTGCCTGCGCCGCGCTCG | 5'-UTR | 29 |
| 6956 | AGGCCTCTCTCCCGCACCTG | 5'-UTR | 30 |
| 6953 | TTCAGTCATTTTCAGCAGGC | AUG | 31 |
| 6952 | TTATATTCAGTCATTTTCAG | AUG | 32 |
| 6951 | CAAGTTTATATTCAGTCATT | AUG | 33 |
| 6950 | GCCTACGCCACCAGCTCCAAC | Codon 12 (wt) | 34 |
| 6949 | CTACGCCACCAGCTCCA | Codon 12 (wt) | 35 |
| 7453 | TACGCCAACAGCTCC | Codon 12 (G→T mutant) | 36 |
| 6948 | GTACTCCTCTTGACCTGCTGT | Codon 61 (wt) | 37 |
| 6947 | CCTGTAGGAATCCTCTATTGT | Codon 38 | 38 |
| 6946 | GGTAATGCTAAAACAAATGC | 3'-UTR | 39 |
| 6945 | GGAATACTGGCACTTCGAGG | 3'-UTR | 40 |
| 7679 | TTTTCAGCAGGCCTCTCTCC | 5'-UTR/AUG | 41 |

*Chimeric oligonucleotides having 2'-O-methyl ends (bold)*

| ISIS # | SEQUENCE (5'->3') | SEQ ID NO: |
|---|---|---|
| 6957 | CAGTGCCTGCGCCGCGCTCG | 29 |
| 7683 | CAGTGCCTGCGCCGCGCTCG | 29 |
| 7679 | TTTTCAGCAGGCCTCTCTCC | 41 |
| 7680 | TTTTCAGCAGGCCTCTCTCC | 41 |

TABLE 9

Phosphorothioate Oligodeoxynucleotides Targeted to Human N-ras

| ISIS # | Sequence (5'->3') | Target Region | SEQ ID NO: |
|---|---|---|---|
| 14677 | CCGGGTCCTAGAAGCTGCAG | 5' UTR | 42 |
| 14678 | TAAATCAGTAAAAGAAACCG | 5' UTR | 43 |
| 14679 | GGACACAGTAACCAGGCGGC | 5' UTR | 44 |
| 14680 | AACAGAAGCTACACCAAGGG | 5' UTR | 45 |
| 14681 | CAGACCCATCCATTCCCGTG | 5' UTR | 46 |
| 14682 | GCCAAGAAATCAGACCCATC | 5' UTR | 47 |
| 14683 | AGGGGGAAGATAAAACCGCC | 5' UTR | 48 |
| 14684 | CGCTTCCATTCTTTCGCCAT | 5' UTR | 49 |
| 14685 | CCGCACCCAGACCCGCCCCT | 5' UTR | 50 |
| 14686 | CAGCCCCCACCAAGGAGCGG | 5' UTR | 51 |
| 14687 | GTCATTTCACACCAGCAAGA | AUG | 52 |
| 14688 | CAGTCATTTCACACCAGCAA | AUG | 53 |
| 14689 | CTCAGTCATTTCACACCAGC | AUG | 54 |
| 14690 | CGTGGGCTTGTTTTGTATCA | Coding | 55 |
| 14691 | CCATACAACCCTGAGTCCCA | 3' UTR | 56 |
| 14692 | CAGACAGCCAAGTGAGGAGG | 3' UTR | 57 |
| 14693 | CCAGGGCAGAAAAATAACAG | 3' UTR | 58 |
| 14694 | TTTGTGCTGTGGAAGAACCC | 3' UTR | 59 |

TABLE 9-continued

Phosphorothioate Oligodeoxynucleotides
Targeted to Human N-ras

| ISIS # | Sequence (5'->3') | Target Region | SEQ ID NO: |
|---|---|---|---|
| 14695 | GCTATTAAATAACAATGCAC | 3' UTR | 60 |
| 14696 | ACTGATCACAGCTATTAAAT | 3' UTR | 61 |

Example 2

Oligonucleotide Synthesis

Substituted and unsubstituted deoxyoligonucleotides were synthesized on an automated DNA synthesizer (Applied Biosystems model 380B) using standard phosphoramidate chemistry with oxidation by iodine. For phosphorothioate oligonucleotides, the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. Synthesis of 2-(amino)adenine-substituted oligonucleotides was carried out in like manner, with the following exception: at positions at which a 2-(amino)adenine is desired, the standard phosphoramidite is replaced with a commercially available 2-aminodeoxyadenosine phosphoramidite (Chemgenes Corp., Waltham, Mass.). After cleavage from the CPG column and deblocking in concentrated ammonium hydroxide at 55° C. (18 hr), the oligonucleotides were purified by precipitation twice out of 0.5 M NaCl solution with 2.5 volumes ethanol. Analytical gel electrophoresis was accomplished in 20% acrylamide, 8 M urea, 454 mM Tris-borate buffer, pH=7.0. Oligonucleotides were judged from polyacrylamide gel electrophoresis to be greater than 80% full-length material.

Oligoribonucleotides were synthesized using the automated synthesizer and 5'-dimethoxy-trityl 2'-tert-butyldimethylsilyl 3'-O-phosphoramidites (American Bionetics, Hayward, Calif.). The protecting group on the exocyclic amines of A, C and G was phenoxyacetyl (Wu et al., *Nucl. Acids Res.* 17:3501, 1989). The standard synthesis cycle was modified by increasing the wait step after the pulse delivery of tetrazole to 900 seconds. Oligonucleotides were deprotected by overnight incubation at room temperature in methanolic ammonia. After drying in vacuo, the 2'-silyl group was removed by overnight incubation at room temperature in 1 M tetrabutylammoniumf luoride (Aldrich Chemical Co., Milwaukee, Wis.) in tetrahydrofuran. Oligonucleotides were purified using a C-18 Sep-Pak cartridge (Waters Corp., Milford, Mass.) followed by ethanol precipitation. Analytical denaturing polyacrylamide electrophoresis demonstrated the RNA oligonucleotides were greater than 90% full length material.

Example 3

Preparation of Sterically Stabilized Liposomes Comprising Antisense Oligonucleotides A. Preparation of Lipid Film Lipid stock solutions were prepared at 20 mg/mL in chloroform. Dipalmitoylphosphatidylcholine (DPPC; Avanti Polar Lipids, Inc., Alabaster, Ala.), cholesterol (Avanti Polar lipids, Inc. or Sigma Chemical Corp., St. Louis, Mo.) and N-(carbamoylmethoxypolyethylene glycol 2000)-1,2-distearoyl-sn-glycero-3-phosphoethanolamine-(DSPE-MPEG$_{2000}$; Avanti Polar Lipids, Inc.) were dispensed into a 30 mL round bottom flask as follows for 150 μmol of total lipid:

TABLE 10

Lipid Components of DSPE-MPEG$_{2000}$ Liposomes
Comprising ISIS 2503

| Component | Mole ratio | Mole % | mg lipid | mL stock lipid solution |
|---|---|---|---|---|
| DPPC | 3 | 57 | 62.74 | 3.137 |
| Cholesterol | 2 | 38 | 22.03 | 1.102 |
| DSPE-MPEG$_{2000}$ | 0.265 | 5 | 20.75 | 1.037 |

Chloroform was removed by evaporation using a rotary evaporator, heating at 60° C. with a moderate vacuum. The lipid material dried as a thin film on the flask wall. Evaporation was continued using high vacuum for an additional 30 minutes at 60° C.

B. Lipid Hydration

Phosphorothioate oligonucleotide (ISIS 2503) was dissolved in water to 100 mg/mL. The solution was made isotonic (80–310 mOsm) with the addition of a small quantity of 5M NaCl as needed. The final solution was filtered through a 0.22 μm membrane. Then, 0.5 mL of the resultant oligo solution was added to the flask containing the lipid film. The flask was rotated at 240 rpm at 60° C. for 5 minutes. The lipid suspension was vortexed heavily to form large multi-lamellar liposomes.

The liposomes were frozen by immersing the flask into a dry ice/acetone bath for 5 minutes. Thawing of the liposomes was accomplished by immersing the flask into a 60° C. water bath as necessary. The preceding freeze/thaw steps were repeated 5 times. The resulting liposome solution appeared "creamy".

C. Particle Sizing

Large multi-lamellar liposomes were converted into near-uniform unilamellar liposomes by either (1) physical extrusion through polycarbonate membranes (Avestin, Inc., Ottawa, Ontario, Canada) of defined porosity (e.g., 100 nm) or microfluidization with a Model 110 S microfluidizer (Microfluidics International Corp., Newton, Mass.). Either technique produces unilamellar liposomes of approximately 90 to about 110 nm in diameter.

D. Liposome Purification

Nonencapsulated oligonucleotide material was separated from the liposomes by gel permeation chromatography using a Superdex-200 column (Pharmacia Biotech, Inc., Piscataway, N.J.) equilibrated in phosphate-buffered saline, pH 7.4. Encapsulation recovery was typically 25–30% and the final ISIS 2503 concentration in the liposomes was about 7 mg/mL. The liposome fractions were pooled and filter-sterilized through a 0.2 μm membrane (Gelman Sciences, Inc., Ann Arbor, Mich.). Liposomes were stored at 4° C.

Example 4

Evaluation of Sterically Stabilized Liposomes Comprising Antisense Oligonucleotides A. Experimental Design and Methods Study Design: Thirteen rhesus monkeys (*Macaca mulatta*) (7 males and 6 females) were used. The animals were pre-pubertal to young adult (in the age range of 3–7 years), and their body weight ranged from 3–4 kg (Table 11). Each animal received a single intravenous infusion of ISIS 2503 encapsulated in sterically stabilized liposomes (10 mg/kg) over approximately 30 minutes. Blood samples for pharmacokinetic analysis were collected prior to dosing and at 0, 1, 2, 6, 12, 24, 40, 60, 96, 120, 144, 168, 192, 240, 384 and 576 hours after dosing. Animals were serial-sacrificed such that 2 animals (1 male and 1 female) were euthanized at each of the following time points from the end of infusion: 24, 60, 120, 168, 384 and 576 hours. An additional male monkey (Animal ID #R4791) died of unknown causes shortly after dosing. Although samples were analyzed for this animal, the values were not included in the pharmacokinetic analysis because the animal died before the earliest study time point. As controls in some experiments, animals were treated in the same manner but with a simple saline formulation of ISIS 2503 in saline.

TABLE 11

Animals Assigned to Study

| Animal ID | Gender | Body Weight (kg) | Time Point (hr) |
| --- | --- | --- | --- |
| R4759 | M | 3.2 | 24 |
| R3524 | F | 4.4 | 24 |
| R4797 | M | 3.7 | 60 |
| R2700 | F | 3.5 | 60 |
| R4778 | M | 3.5 | 120 |
| R4784 | F | 3.6 | 120 |
| R4758 | M | 3.6 | 168 |
| R4781 | F | 3.6 | 168 |
| R4796 | M | 3.1 | 384 |
| R4782 | F | 3.5 | 384 |
| R4764 | M | 4.2 | 576 |
| R4768 | F | 3.5 | 576 |

A full necropsy was conducted on all animals. The following tissues were collected from each animal: brain, heart, pancreas, prostate, ovaries, spleen, intestine, kidney cortex, kidney medulla, liver, mesenteric and mandibular (combined, M & M) lymph nodes, axillary and inguinal (combined, A & I) lymph nodes, lung, back skin, and hand skin. Whole blood and tissue samples were extracted and analyzed by capillary gel electrophoresis (CGE).

Sample Extraction in Whole Blood: Blood samples were vortexed and an aliquot (100 μl) was measured into a 2 mL Fastprep tube (BIO101, Inc., Vista, Calif.) containing approximately ¼ inch of homogenization beads. Following the addition of 390 μL PBS, 5 μL 10% NP-40, and 5 μL 100 μM $T_{27}$ (a 27-mer phosphorothioate oligodeoxythimidine used as the internal standard), the mixture was homogenized in a Savant Tissue Disrupter (BIO101, Inc., Vista, Calif.). The samples were then extracted with phenol-chloroform to remove proteins and lipids; oligonucleotides remained in the aqueous phase. To enhance the separation of the aqueous phase from the organic phase, an aliquot of phase lock gel (Intermountain Scientific Corp., Kaysville, Utah) was added to the samples after adding phenol-chloroform. The phenol-chloroform layer was back-extracted with 500 μL of water and the aqueous phases were pooled. The aqueous phase was then evaporated to dryness, resuspended with 5 mL SAX loading buffer (containing 10 mM Tris-HCl, 0.5 M KCl, and 20% acetonitrile, at pH 9.0) in preparation for solid phase extraction.

Sample Extraction in Tissue: The method for tissue sample extraction combined the proteinase K digestion method previously used for extraction of oligonucleotides from tissues (Cossum et al., *J. Pharmacol. Exp. Therap.* 269:89, 1994) with the solid phase extraction method (Leeds et al., *Analytical Biochem.* 235:36, 1996). Monkey tissues were weighed, homogenized in a Bio Savant, and incubated for 24 hours at 37° C. in a 2.0 mg/mL proteinase K solution of digestion buffer consisting of 0.5% Non-Idet P-40 (NP-40) with 20 mM Tris-HCl (pH 8.0), 20 mM EDTA, and 100 mM NaCl. An appropriate amount of $T_{27}$ ranging from 0.5 to 10 μM, was added for quantitation by capillary electrophoresis. The aqueous layer was then extracted with phenol-chloroform, the phenol-chloroform layer was back-extracted with 500 μL of water and the aqueous phases were pooled. The aqueous layer was extracted again with chloroform to remove the phenol. Samples were then evaporated to dryness, resuspended in 200 μl concentrated ammonium hydroxide and incubated at 55° C. for 12 to 24 hours. The samples were then re-evaporated to dryness, resuspended with 5 mL SAX loading buffer (containing 10 mM Tris-HCl, 0.25 M KCl, and 20% acetonitrile, at pH 9.0) in preparation for solid phase extraction.

Solid Phase Extraction: After phenol-chloroform extraction, both blood and tissue samples were further extracted using a J&W Scientific, Inc. (Folson, Calif.) strong anion exchange (SAX) SPE column. For solid phase extraction, the column was prepared for use by wetting it with 1 ml of acetonitrile followed by 1 ml of distilled water. The column was then equilibrated with 3 ml of loading buffer prior to loading the tissue or blood extracts. After loading the extracts, the anion exchange SPE column was washed with 3 mL of the loading buffer, and the oligonucleotides were eluted with 3 mL of elution buffer (containing 10 mM Tris-HCl, 0.5 M KCl, and 1.0 M NaBr, and 30% acetonitrile, at pH 9.0). The eluted samples were diluted and were then desalted using a reversed-phase solid phase extraction column.

The reversed-phase solid phase extraction column (Isolute, from Alltech Associates, Inc., Deerfield, Ill.) was pre-equilibrated with 1 mL acetonitrile, 1 mL distilled water, and 3 mL eluting buffer (10 mM Tris-HCl, 0.5 M KCl, and 1.0 M NaBr, at pH 9.0). After the diluted eluate from the anion exchange column was loaded onto reverse phase SPE column, it was washed with 5 mL of distilled water, and purified oligonucleotide was then eluted using 3 mL of fresh 20% acetonitrile in distilled water. After evaporation to dryness, the samples were resuspended in 40 μl distilled water, and a 15 μl aliquot was desalted by dialysis on a Millipore VS membrane (pore size 0.025 microns, Millipore Corp., Bedford, Mass.) floating in a 60×15 mm polystyrene petrie dish (Becton Dickinson and Co., Lincoln Park, N.J.) containing distilled water prior to loading into microvials for analysis by capillary electrophoresis.

Capillary Electrophoresis: A Beckman P/ACE Model 5010 capillary electrophoresis instrument (Beckman Instruments, Inc., Fullerton, Calif.) was used for gel-filled capillary electrophoresis analysis. Samples were electrokinetically injected using an applied voltage between 3–10 kV for a duration ranging from 3–20 seconds. Length-based separation of the oligonucleotides was achieved by using a coated-capillary (Bio-Rad Laboratory, Hercules, Calif.) with Beckman eCAP ssDNA 100-R Gel. Separation was optimized using a constant applied voltage of 20 kV and a temperature of 40° C. Oligonucleotide peaks were detected by UV absorbance at 260 nm. Beckman System Gold Software on the P/ACE instrument was used to determine the areas under the curve for oligonucleotide peaks in the resultant electropherograms. A peak area threshold of 0.01 area units and minimum peak width of 0.08 min were the standard integration parameters (Leeds et al., *Analytical Biochem.* 235:36, 1996).

Quantitation: Quantitation of intact ISIS 2503 and metabolites for whole blood samples was based on the calibration curve with $T_{27}$ as the internal standard. The limit of quantitation for this assay has been estimated to be 0.10 µg/mL oligonucleotide in blood. In contrast, the concentrations of ISIS 2503 and metabolites in the tissue samples were calculated from the ratio of the absorbencies, based only on the starting concentration of internal standard ($T_{27}$) added to the samples using the following equation:

$$C_2 = C_1(E_1/E_2)[(A_2 T_{m2})/(A_1 T_{m1})]$$

Where $C_1$=concentration of the internal standard, $C_2$=concentration of the analyte (ISIS 2503 or metabolites), $E_1$=molar extinction coefficient of the internal standard, $E_2$=molar extinction coefficient of the analyte, $A_1$=area of the internal standard peak, $A_2$=area of the analyte peak, $T_{m1}$=migration time of the internal standard peak, and $T_{m2}$=migration time of the analyte peak.

Calculations of extinction coefficients for ISIS 2503, metabolites, and $T_{27}$ are made using a program which calculates the sums of the extinction coefficients from the individual bases according to the base composition. For the calculation of extinction coefficients, metabolites are assumed, to be generated by loss of nucleotide from the 3'-end. The limit of quantitation for this assay has been estimated to be 0.10 µg/g oligonucleotide in tissue.

Pharmacokinetic Analysis: Inspection of the semilogarithmic plots of intact ISIS 2503 (full length) blood level-versus time curves indicated that they could be described by a monoexponential equation. First order elimination was assumed. Initial estimates of parameters were obtained by linear regression of the terminal concentration time points. Nonlinear regression was accomplished using a one compartment model for each individual animal (WinNonlin 1.0, Scientific Consulting, Inc., Apex, N.C.). A uniform weight of 1 was used for all blood-level data. Four of the animals were excluded from complete individual pharmacokinetic analysis of blood concentrations because they were sacrificed before a complete blood profile could be collected (2 at 24 hours and 2 at 60 hours).

Tissue elimination was analyzed by noncompartmental methods using WinNonlin 1.0. Tissue half-lives were estimated by linear regression analysis of the log-linear terminal phase of the tissue concentration-time curve. The area under the tissue concentration-time curve ($AUC_{0 \to \infty}$) and the area under the first moment of the concentration-time curve ($AUMC_{0 \to \infty}$) were calculated using the linear trapezoidal rule, up to the last measured time point, plus the extrapolated area. The mean residence time (MRT) was calculated as the ratio of the $AUMC_{(0 \to \infty)}$ to the $AUC_{(0 \to \infty)}$.

Statistics: Statistical analysis for gender difference of kinetic parameters was performed by F-test (Excel 6.0, Microsoft Corp., Redmond, Wash.) for the analysis of variance, and t-test (Excel 6.0) for the analysis of mean at the p=0.05 level. Descriptive statistics were used to present data summaries for pharmacokinetic parameter estimates and blood concentration data.

B. Results

Figure 6A:
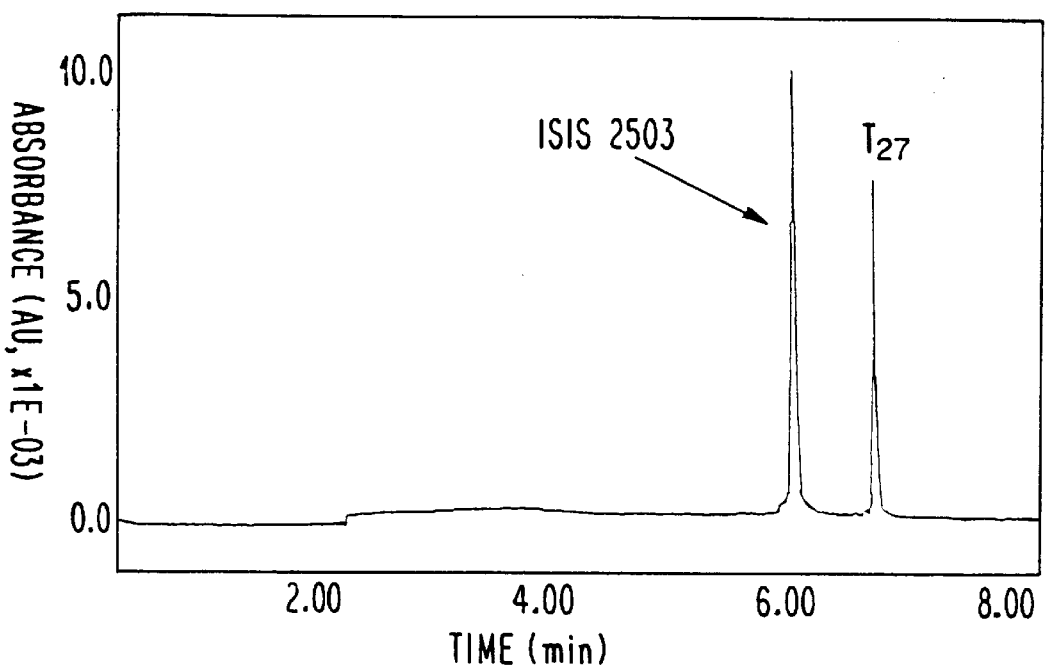
FIGS. 6A and 6B are representative electropherograms of a liposomal (FIG. 6A) or saline formulation (FIG. 6B) of ISIS 2503 in monkey blood samples. Samples were taken 60 hours (a) after an 0.5 hour infusion or (b) 1 hour after initiation of a 2-hour infusion of 10 mg/kg of the respective formulations. Peaks corresponding to ISIS 2503 and various metabolites (arrows) or to an internal standard ($T_{27}$, a 27-mer phosphorothioate oligodeoxythymidine) are indicated.
Figure 6B:
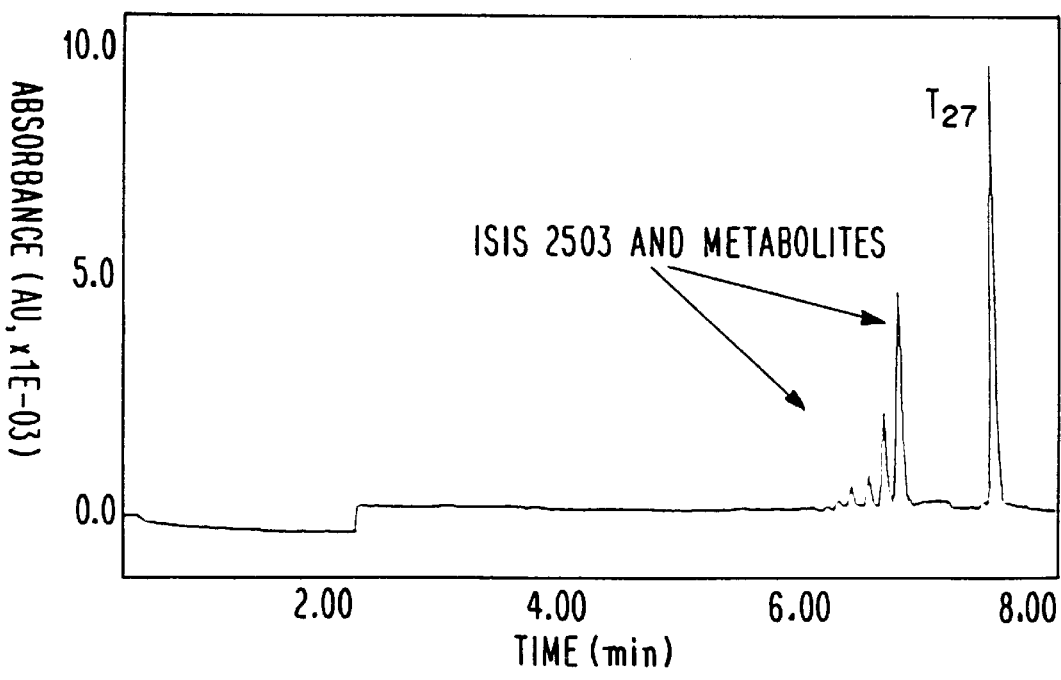
Figure 7A:
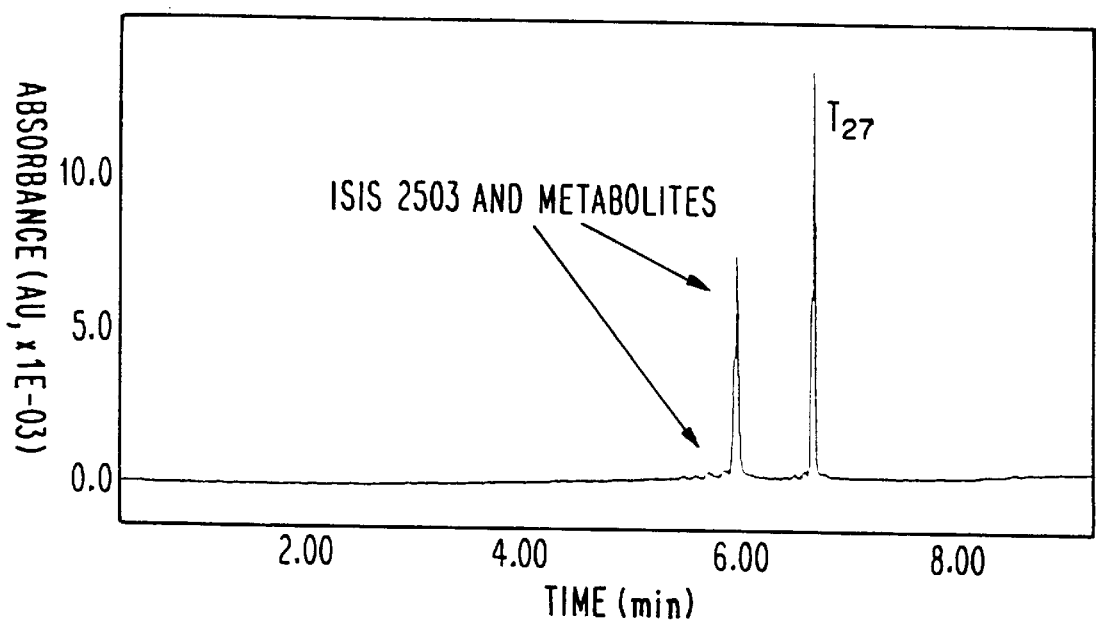
FIGS. 7A and 7B are representative electropherograms of a liposomal (FIG. 7A) or saline formulation (FIG. 7B) of ISIS 2503 in monkey kidney cortex samples. Samples were taken 60 hours (a) after an 0.5 hour infusion or (b) 48 hours after the last 2-hour infusion of 14 total doses administered every other day of 10 mg/kg of the respective formulations. Peaks corresponding to ISIS 2503 and various metabolites (arrows), including a suspected (n+1) species (see Examples), or to an internal standard ($T_{27}$, a 27-mer phosphorothioate oligodeoxythymidine) are indicated.
Figure 7B:
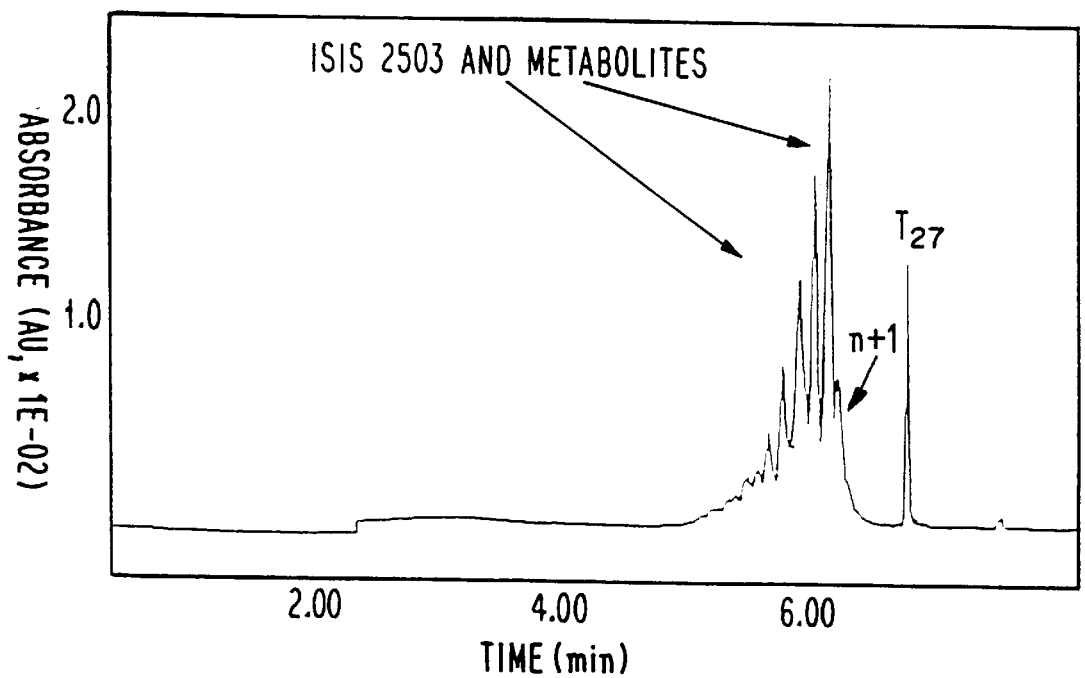

Blood Pharmacokinetics and Metabolism: FIGS. 6 and 7 are representative electropherograms of (a) liposomal and (b) saline formulations of ISIS 2503 in blood and kidney samples, respectively, from monkeys after i.v. infusions of 10 mg/kg of the respective formulations. The saline formulated oligonucleotide samples were taken either 1 hour after initiation of a 2-hour infusion in the case of plasma or 48 hours after the last 2-hour infusion of 14 doses administered every other day (q2d). In contrast, the liposomal oligonucleotide formulations were evaluated at 60 hours after an 0.5 hour infusion. Despite the longer period during which the liposomal oligonucleotide formulations were exposed to degradative processes in the tissues, the ISIS 2503 remained in a significantly more intact state than the saline-formulated oligonucleotide (as can be seen by comparing panel (a) in FIGS. 6 and 7 to panel (b)).

The time course of the clearance of ISIS 2503 and oligonucleotide metabolites from blood after administration of the liposomal oligonucleotide composition is prolonged (see Tables 12 and 13 and FIG. 1). Maximum blood concentration ($C_{max}$) of intact ISIS 2503 was approximately 90 µg/mL and was observed at the end of the 30-minute infusion. ISIS 2503 concentration did not decrease by 1 hour after infusion but remained at c. 90 µg/mL). Concentrations in blood decreased slowly to approximately 10 µg/mL at 144 hours after infusion. In these experiments, the method for quantitating ISIS 2503 concentrations in blood or tissues does not distinguish between free and liposome encapsulated oligonucleotides, and both parent compound and total oligonucleotide concentrations are presented because many of the chain-shortened metabolites retain physical and chemical properties similar to those of the parent compound ISIS 2503 and thus may potentially have some biological activity.

Pharmacokinetic parameter estimates for males and females were averaged since statistical analysis indicated no significant gender differences. The mean blood half-life for intact ISIS 2503 was 57.2 hours (Table 14). The concentration of ISIS 2503 in blood generally fell below the limit of detection after 168 hours. The observed concentrations in blood were less well predicted by the model after 120 hours (FIG. 1). The values predicted by the model were higher than the actual values observed at the late time points suggesting that there were alterations in the kinetics after extended circulation times. This phenomenon may be a result of the loss of liposome integrity after prolonged circulation in blood. The average total body clearance and $Vd_{ss}$ were 1.53±0.28 mL/hr/kg and 123±28 mL/kg, respectively. The volume of distribution was larger than the blood compartment (73.4 mL/kg) indicating some distribution into tissues, but also indicated a large portion of administered dose remained in the general circulation (Davies et al., *Pharm. Res.* 10:1093, 1993).

The metabolites of ISIS 2503 in blood co-migrated on CGE with ISIS 2503 shortened by removal of 1 or 2 bases (19-mer and 18-mer; in Tables 12, 13 and 15 these are referred to as "n–1" and "n–2," respectively). Concentrations of metabolites observed were an order of magnitude lower than that of parent drug. The chain-shortened metabolites cumulatively represented approximately 5 to 20% of the total oligonucleotides in blood. There was only a small increase in the percentage of oligonucleotide metabolites with time. This pattern of very low concentrations of metabolites observed in blood suggests that liposomal encapsulation protected the oligonucleotide from blood (and tissue) nucleases that might otherwise rapidly metabolize the circulating oligonucleotide, and supports the notion that there was very little leakage of ISIS 2503 from the liposome.

TABLE 12

Concentrations (μg/mL) of ISIS 2503 and All Detected Metabolites in Blood After 0.5 hr Intravenous Infusion of 10 mg/kg ISIS 2503 Encapsulated in Sterically Stabilized Liposomes to Rhesus Monkeys

| Time (hr) | No. of Animals | Mean Concentration (μg/mL) ISIS 2503 | n-1 | n-2 | Total | % Full Length |
|---|---|---|---|---|---|---|
| 0 | 12 | 89.0[a] (24.7)[b] | 4.27 (3.54) | nd | 93.3 (25.4) | 95.5 (3.5) |
| 1 | 12 | 90.4 (18.9) | 3.44 (2.24) | 0.28 (0.96) | 94.1 (20.0) | 96.1 (2.5) |
| 2 | 12 | 82.1 (22.0) | 3.27 (2.10) | nd | 85.4 (22.2) | 96.1 (2.6) |
| 6 | 12 | 78.3 (20.4) | 2.92 (1.64) | 0.31 (1.06) | 81.5 (20.6) | 96.0 (2.6) |
| 12 | 12 | 64.6 (18.7) | 1.35 (1.58) | 0.28 (0.96) | 66.2 (19.7) | 97.8 (2.9) |
| 24 | 12 | 63.3 (18.2) | 2.08 (1.26) | nd | 65.4 (18.3) | 96.7 (2.2) |
| 40 | 10 | 50.1 (15.0) | 1.45 (1.02) | 0.06 (0.17) | 51.9 (15.4) | 96.9 (1.8) |
| 60 | 10 | 50.6 (9.5) | 1.37 (1.02) | 0.29 (0.91) | 56.7 (16.6) | 92.2 (14.0) |
| 96 | 8 | 22.6 (12.9) | 2.65 (2.23) | nd | 25.3 (14.6) | 91.9 (7.2) |
| 120 | 7 | 15.7 (10.2) | 2.61 (1.91) | nd | 18.3 (12.0) | 89.2 (8.0) |
| 144 | 4 | 10.6 (6.3) | 1.07 (2.14) | nd | 11.7 (7.4) | 94.2 (11.6) |
| 168 | 4 | 4.42 (1.32) | 0.40 (0.69) | nd | 4.82 (1.67) | 93.5 (11.3) |
| 192 | 2 | 3.62 | 0.59 (0.83) | nd | 4.21 (0.60) | 84.4 (22.0) |
| 240 | 1 | 2.13 | 1.19 | nd | 3.32 | 64.2 |

"% Full-length" = percent of total detectable oligonucleotide represented by intact ISIS 2503.
"nd" = not detected (detection level = 0.10 μg/mL).
[a]Mean value.
[b]Standard deviation.

TABLE 13

ISIS 2503 and Total Oligonucleotide Whole Blood Concentrations after 0.5 hr i.v. Infusion of 10 mg/kg ISIS 2503 Encapsulated in Sterically Stabilized Liposomes to Rhesus Monkeys (Average of Duplicate Analysis)

| Animal ID # | Gender | Time[a] (hr) | μg/mL (ISIS 2503) | n-1 | n-2 | n-3 | Total | % Full[b] |
|---|---|---|---|---|---|---|---|---|
| R4759 | M | 0 | 115 | 1.06 | nd | nd | 116 | 99.1 |
| R4759 | M | 1 | 120 | 6.58 | 3.32 | nd | 130 | 92.4 |
| R4759 | M | 2 | 93.8 | 6.11 | nd | nd | 99.9 | 93.9 |
| R4759 | M | 6 | 89.8 | 5.71 | 3.66 | nd | 99.2 | 90.6 |
| R4759 | M | 12 | 78.7 | 5.30 | 3.33 | nd | 87.3 | 90.1 |
| R4759 | M | 24 | 58.9 | 4.09 | nd | nd | 63.0 | 93.5 |
| R3524 | F | 0 | 131 | 1.11 | nd | nd | 132 | 99.2 |
| R3524 | F | 1 | 92.2 | 0.33 | nd | nd | 92.5 | 99.6 |
| R3524 | F | 2 | 92.9 | 0.58 | nd | nd | 93.5 | 99.4 |
| R3524 | F | 6 | 102 | 0.90 | nd | nd | 103 | 99.1 |
| R3524 | F | 12 | 98.8 | 0.77 | nd | nd | 99.6 | 99.2 |
| R3524 | F | 24 | 76.4 | 0.11 | nd | nd | 76.5 | 99.9 |
| R4797 | M | 0 | 84.5 | 6.33 | nd | nd | 90.8 | 93.0 |
| R4797 | M | 1 | 85.1 | 6.42 | nd | nd | 91.5 | 93.0 |
| R4797 | M | 2 | 71.4 | 6.30 | nd | nd | 77.7 | 91.9 |
| R4797 | M | 6 | 66.1 | 3.65 | nd | nd | 69.8 | 94.8 |
| R4797 | M | 12 | 68.5 | nd | nd | nd | 68.5 | 100 |
| R4797 | M | 24 | 53.8 | 3.17 | nd | nd | 56.9 | 94.4 |
| R4797 | N | 40 | 40.4 | 0.89 | nd | nd | 41.3 | 97.8 |
| R4797 | M | 60 | 51.4 | 0.49 | nd | nd | 96.3 | 53.4 |
| R2700 | F | 0 | 75.7 | 6.61 | nd | nd | 82.3 | 92.0 |
| R2700 | F | 1 | 82.1 | 6.62 | nd | nd | 88.7 | 92.5 |
| R2700 | F | 2 | 64.9 | 6.15 | nd | nd | 71.1 | 91.3 |
| R2700 | F | 6 | 68.8 | 6.03 | nd | nd | 74.8 | 91.9 |
| R2700 | F | 12 | 45.1 | nd | nd | nd | 45.1 | 100 |
| R2700 | F | 24 | 58.7 | 1.48 | nd | nd | 60.2 | 97.5 |
| R2700 | F | 40 | 44.4 | 1.34 | 0.55 | nd | 46.3 | 95.9 |
| R2700 | F | 60 | 61.3 | 0.72 | nd | nd | 62.0 | 98.8 |
| R4778 | M | 0 | 96.3 | 10.3 | nd | nd | 107 | 90.3 |
| R4778 | M | 1 | 124 | 1.58 | nd | nd | 126 | 98.7 |
| R4778 | M | 2 | 133 | 2.59 | nd | nd | 135 | 98.1 |
| R4778 | M | 6 | 128 | 2.78 | nd | nd | 131 | 97.9 |
| R4778 | M | 12 | 94.7 | 2.60 | nd | nd | 97.3 | 97.3 |
| R4778 | N | 24 | 106 | 2.05 | nd | nd | 108 | 98.1 |
| R4778 | M | 40 | 44.6 | 1.52 | nd | nd | 46.1 | 96.7 |
| R4778 | M | 60 | 42.3 | 1.03 | nd | nd | 43.4 | 97.6 |
| R4778 | M | 96 | 5.03 | nd | nd | nd | 5.03 | 100 |
| R4784 | F | 0 | 92.9 | 10.5 | nd | nd | 103 | 89.8 |
| R4784 | F | 1 | 89.6 | 1.94 | nd | nd | 91.5 | 97.9 |
| R4784 | F | 2 | 95.0 | 1.96 | nd | nd | 96.9 | 98.0 |
| R4784 | F | 6 | 85.0 | 1.34 | nd | nd | 86.3 | 98.5 |
| R4784 | F | 12 | 45.7 | nd | nd | nd | 45.7 | 100 |
| R4784 | F | 24 | 70.9 | 2.05 | nd | nd | 72.9 | 97.2 |
| R4784 | F | 40 | 48.3 | nd | nd | nd | 91.5 | 97.9 |
| R4784 | F | 60 | 53.4 | 0.97 | nd | nd | 54.3 | 98.2 |
| R4784 | F | 96 | 43.5 | 3.99 | nd | nd | 47.4 | 91.6 |
| R4784 | F | 120 | 23.3 | 3.45 | nd | nd | 26.8 | 87.1 |
| R4758 | M | 0 | 109 | 4.91 | nd | nd | 114 | 95.7 |
| R4758 | M | 1 | 78.1 | 3.08 | nd | nd | 81.2 | 96.2 |
| R4758 | M | 2 | 69.0 | 2.60 | nd | nd | 71.6 | 96.4 |
| R4758 | M | 6 | 75.1 | 2.99 | nd | nd | 78.1 | 96.2 |
| R4758 | M | 12 | 62.4 | 0.87 | nd | nd | 63.3 | 98.6 |
| R4758 | M | 24 | 85.6 | 3.35 | nd | nd | 89.0 | 96.2 |
| R4758 | M | 40 | 48.1 | 1.22 | nd | nd | 49.3 | 97.5 |
| R4758 | M | 60 | 52.1 | 0.71 | nd | nd | 52.8 | 98.7 |
| R4758 | M | 96 | 32.2 | 4.78 | nd | nd | 37.0 | 87.1 |
| R4758 | M | 120 | 18.3 | 2.48 | nd | nd | 20.8 | 88.1 |
| R4758 | M | 144 | 17.3 | nd | nd | nd | 17.3 | 100 |
| R4758 | M | 168 | 11.8 | nd | nd | nd | 11.8 | 100 |
| R4781 | F | 0 | 90.6 | 4.07 | nd | nd | 94.6 | 95.7 |
| R4781 | F | 1 | 96.1 | 4.24 | nd | nd | 100 | 95.8 |
| R4781 | F | 2 | 105 | 5.26 | nd | nd | 110 | 95.2 |
| R4781 | F | 6 | 67.1 | 3.12 | nd | nd | 70.2 | 95.6 |
| R4781 | F | 12 | 43.9 | nd | nd | nd | 43.9 | 100 |
| R4781 | F | 24 | 53.4 | 2.66 | nd | nd | 56.0 | 95.3 |
| R4781 | F | 40 | 51.8 | 1.57 | nd | nd | 53.4 | 97.1 |
| R4781 | F | 60 | 52.9 | 0.85 | nd | nd | 53.8 | 98.4 |
| R4781 | F | 96 | 26.0 | 4.48 | nd | nd | 30.5 | 85.3 |
| R4781 | F | 120 | 15.5 | 4.28 | nd | nd | 19.7 | 78.3 |
| R4781 | F | 144 | 3.46 | nd | nd | nd | 3.46 | 100 |
| R4781 | F | 168 | 2.93 | nd | nd | nd | 2.93 | 100 |
| R4782 | M | 0 | 30.9 | 0.30 | nd | nd | 31.2 | 99.1 |
| R4782 | M | 1 | 72.4 | 1.42 | nd | nd | 73.8 | 98.1 |
| R4782 | M | 2 | 60.4 | 1.16 | nd | nd | 61.5 | 98.1 |
| R4782 | M | 6 | 62.1 | 1.32 | nd | nd | 63.4 | 97.9 |
| R4782 | M | 12 | 58.3 | 1.05 | nd | nd | 59.4 | 98.2 |
| R4782 | M | 24 | 51.8 | 0.89 | nd | nd | 52.7 | 98.3 |
| R4782 | M | 40 | 37.5 | 2.56 | nd | nd | 40.1 | 93.6 |
| R4782 | M | 60 | 43.8 | 3.84 | 2.89 | nd | 50.5 | 86.7 |
| R4782 | M | 96 | 26.8 | 3.50 | nd | nd | 30.3 | 88.5 |
| R4782 | M | 120 | 19.1 | 3.52 | nd | nd | 22.6 | 84.4 |
| R4782 | M | 144 | 14.1 | 4.27 | nd | nd | 18.4 | 76.8 |
| R4782 | M | 168 | 5.45 | nd | nd | nd | 5.45 | 100 |
| R4782 | M | 192 | 4.64 | nd | nd | nd | 4.64 | 100 |
| R4796 | F | 0 | 76.1 | 2.70 | nd | nd | 78.8 | 96.6 |
| R4796 | F | 1 | 106 | 4.74 | nd | nd | 111 | 95.7 |
| R4796 | F | 2 | 64.1 | 2.36 | nd | nd | 66.4 | 96.5 |
| R4796 | F | 6 | 73.4 | 3.23 | nd | nd | 76.6 | 95.8 |
| R4796 | F | 12 | 63.0 | 1.40 | nd | nd | 64.4 | 97.8 |
| R4796 | F | 24 | 49.1 | 0.89 | nd | nd | 50.0 | 98.2 |
| R4796 | F | 40 | 43.1 | 2.13 | nd | nd | 45.2 | 95.3 |
| R4796 | F | 60 | 43.7 | 1.21 | nd | nd | 44.9 | 97.3 |
| R4796 | F | 96 | 21.1 | 4.44 | nd | nd | 25.5 | 82.6 |
| R4796 | F | 120 | 29.3 | 4.58 | nd | nd | 33.8 | 86.5 |
| R4796 | F | 144 | 7.42 | nd | nd | nd | 7.42 | 100 |

TABLE 13-continued

ISIS 2503 and Total Oligonucleotide Whole Blood
Concentrations after 0.5 hr i.v. Infusion of 10 mg/kg ISIS 2503
Encapsulated in Sterically Stabilized Liposomes to
Rhesus Monkeys (Average of Duplicate Analysis)

| Animal ID # | Gender | Time[a] (hr) | μg/mL (ISIS 2503 | n-1 | n-2 | n-3 | Total | % Full[b] |
|---|---|---|---|---|---|---|---|---|
| R4796 | F | 168 | 4.89 | 1.19 | nd | nd | 6.08 | 80.4 |
| R4796 | F | 192 | 2.61 | 1.18 | nd | nd | 3.79 | 68.9 |
| R4796 | F | 240 | 2.13 | 1.19 | nd | nd | 3.32 | 64.2 |
| R4768 | F | 0 | 80.5 | 1.68 | nd | nd | 82.1 | 98.0 |
| R4768 | F | 1 | 76.4 | 1.35 | nd | nd | 77.8 | 98.3 |
| R4768 | F | 2 | 72.2 | 1.30 | nd | nd | 73.5 | 98.2 |
| R4768 | F | 6 | 69.6 | 1.46 | nd | nd | 71.0 | 97.9 |
| R4768 | F | 12 | 69.4 | 1.31 | nd | nd | 70.7 | 98.1 |
| R4768 | F | 24 | 50.4 | 0.84 | nd | nd | 51.3 | 98.4 |
| R4768 | F | 40 | 90.6 | 3.25 | nd | nd | 93.8 | 96.5 |
| R4768 | F | 60 | 68.7 | 2.44 | nd | nd | 71.1 | 96.6 |
| R4768 | F | 96 | 5.61 | nd | nd | nd | 5.61 | 100 |
| R4768 | F | 120 | 3.24 | nd | nd | nd | 3.24 | 100 |
| R4764 | M | 0 | 85.7 | 1.64 | nd | nd | 87.4 | 98.1 |
| R4764 | M | 1 | 61.8 | 2.99 | nd | nd | 64.8 | 95.4 |
| R4764 | M | 2 | 63.9 | 2.89 | nd | nd | 66.8 | 95.7 |
| R4764 | M | 6 | 52.8 | 2.57 | nd | nd | 55.4 | 95.4 |
| R4764 | M | 12 | 46.7 | 2.88 | nd | nd | 49.6 | 94.2 |
| R4764 | M | 24 | 44.5 | 3.35 | nd | nd | 47.8 | 93.0 |
| R4764 | M | 40 | 52.0 | nd | nd | nd | 52.0 | 100 |
| R4764 | M | 60 | 37.0 | 1.40 | nd | nd | 38.4 | 96.4 |
| R4764 | M | 96 | 20.8 | nd | nd | nd | 20.8 | 100 |
| R4764 | M | 120 | 1.16 | nd | nd | nd | 1.16 | 100 |

"nd" = not detected
[a]Time is given in hours.
[b]"%Full" = % full-length oligonucleotide detected.

TABLE 14

Summary of Estimated Pharmacokinetic parameters
(n = 8) for ISIS 2503 (10 mg/kg) Encapsulated
in Sterically Stabilized Liposomes Administered
to Rhesus Monkeys by 0.5 hr Infusion

| Parameter | Mean | SD | CV %[b] |
|---|---|---|---|
| AUC (μg•hr/mL) | 6760 | 1240 | 18.4 |
| $K_{10}$-$t_{1/2}$ (hr) | 57.2 | 14.2 | 24.9 |
| Cmax (μg/mL)[a] | 90.4 | 23.0 | 26.9 |
| Cl (mL/hr/kg) | 1.52 | 0.28 | 18.3 |
| MRT (hr) | 82.5 | 20.5 | 24.9 |
| $Vd_{SS}$ (mL/kg) | 123 | 28 | 22.3 |

[a]Data obtained from 12 animals.
[b]CV% = Coefficient of Variation = (Standard deviation / Mean) × 100.

In sum, encapsulation of phosphorothioate oligonucleotide into liposomes greatly modified oligonucleotide pharmacokinetics. ISIS 2503 in liposomes was cleared slowly from the blood compared with previous experience with unencapsulated oligonucleotide. Phosphorothioate oligonucleotide concentration following intravenous infusion of unencapsulated oligonucleotide in monkeys decreases rapidly from circulation with an average distribution half-life of 36–83 minutes (Agrawal et al., *Clinical Pharmacokinet.* 28:7, 1995). In contrast, the distribution phase half-life of ISIS 2503 in this liposome formulation was markedly longer (approximately 57 hours), and resulted in an AUC that was approximately 70-fold greater than an equivalent dose of an unencapsulated oligonucleotide.

Tissue Distribution, Elimination Kinetics and Metabolism: ISIS 2503 was distributed widely into all the tissues analyzed. The highest tissue concentrations of total oligonucleotide were measured in liver, with slightly lower concentrations detected in spleen, followed by the lymph nodes, lung, hand skin, kidney cortex and medulla, heart, back skin, pancreas, colon, and brain (Table 15, FIGS. 2–5). It appears that the primary organs of ISIS 2503 distribution were the organs of the reticulo-endothelial system. Largest sample to sample variability was observed in skin where, presumably, the thickness of the skin layer collected varied greatly. Tissue distribution was also greatly different for the liposome formulation compared with unencapsulated oligonucleotides studied previously (Agrawal et al., *Clinical Pharmacokinet.* 28:7, 1995; Cossum et al., *J. Pharmacol. Exp. Therap.* 267:1181, 1993), where the highest concentration of oligonucleotide is consistently observed in kidney.

Relatively long half-lives of ISIS 2503 were observed in all tissues studied (Table 16). The mean residence time (15 days) of ISIS 2503 in the kidney cortex was the longest among all the tissues examined. This slow clearance may represent slow metabolism in the kidney or, alternatively, the kidney may take up free oligonucleotide from the circulation as it is slowly released from liposomes, thus giving the appearance of prolonged half-life. Uptake was slow in all tissues with a time to peak concentration from 1 to 7 days. The concentration of ISIS 2503 in brain, prostate, and ovaries was still increasing up to seven days after dosing. However, the concentration of ISIS 2503 in these tissues was below the limit of quantitation for the CGE analysis by 384 hours (the next data point after the 7-day time point).

TABLE 15

Average (n = 2) Tissue Concentrations (μg/g) of ISIS 2503
and All Detected Metabolites After 0.5 hr Intravenous
Infusion of 10 mg/kg ISIS 2503 Encapsulated in Sterically
Stabilized Liposomes to Rhesus Monkeys

| Time (hr) | (μg/mL) 2503 | n + 1 | n − 1 | n − 2 | n − 3 | n − 4 | n − 5 | n − 6 | Total | % Full Length |
|---|---|---|---|---|---|---|---|---|---|---|
| | | | | Kidney Cortex | | | | | | |
| 24 | 0.37 | 13.4 | 0.73 | 0.38 | 0.46 | 0.24 | 0.11 | 0.07 | 15.7 | 77.2 |
| 60 | 0.24 | 11.2 | 0.61 | 0.34 | 0.13 | 0.09 | 0.05 | 0.04 | 12.7 | 88.7 |
| 120 | 0.12 | 4.87 | 0.44 | 0.38 | 0.38 | 0.17 | 0.20 | 0.06 | 6.66 | 72.1 |
| 168 | 0.18 | 6.00 | 0.72 | 0.22 | 0.94 | 0.48 | 0.36 | 0.16 | 9.31 | 66.2 |
| 384 | 0.13 | 1.97 | 0.36 | 0.43 | 0.52 | 0.39 | 0.22 | 0.10 | 4.35 | 45.3 |
| 576 | 0.07 | 0.90 | 0.19 | 0.20 | 0.09 | nd | nd | nd | 1.45 | 62.1 |

TABLE 15-continued

Average (n = 2) Tissue Concentrations (μg/g) of ISIS 2503 and All Detected Metabolites After 0.5 hr Intravenous Infusion of 10 mg/kg ISIS 2503 Encapsulated in Sterically Stabilized Liposomes to Rhesus Monkeys

| Time (hr) | (μg/mL) 2503 | n + 1 | n − 1 | n − 2 | n − 3 | n − 4 | n − 5 | n − 6 | Total | % Full Length |
|---|---|---|---|---|---|---|---|---|---|---|
| Kidney Medulla ||||||||||
| 24 | 0.47 | 14.3 | 0.33 | 0.08 | 0.17 | 0.18 | 0.07 | nd | 15.6 | 92.6 |
| 60 | 0.16 | 13.3 | 0.51 | 0.15 | 0.28 | 0.11 | 0.05 | 0.09 | 14.8 | 91.3 |
| 120 | 0.18 | 7.48 | 0.53 | 0.39 | 0.40 | 0.28 | 0.29 | 0.11 | 10.1 | 73.2 |
| 168 | 0.38 | 7.17 | 0.69 | 0.39 | 0.54 | 0.38 | 0.23 | 0.14 | 10.6 | 67.8 |
| 384 | 0.06 | 2.40 | 0.33 | 0.41 | 0.17 | 0.12 | 0.21 | 0.21 | 4.05 | 59.3 |
| 576 | 0.05 | 0.93 | 0.32 | 0.26 | 0.24 | 0.06 | 0.05 | 0.06 | 1.99 | 46.7 |
| Liver ||||||||||
| 24 | 0.87 | 46.7 | 2.22 | 0.65 | 0.99 | 0.44 | 0.15 | 0.03 | 52.1 | 90.0 |
| 60 | 0.22 | 94.1 | 4.60 | 1.78 | 2.73 | 0.93 | 0.59 | 0.47 | 119 | 80.0 |
| 120 | 0.50 | 88.9 | 7.17 | 3.22 | 4.55 | 1.71 | 1.13 | 1.09 | 110 | 80.9 |
| 168 | 0.91 | 106 | 10.2 | 4.62 | 7.59 | 2.76 | 1.94 | 1.64 | 140 | 72.8 |
| 384 | 0.28 | 13.45 | 3.27 | 1.76 | 3.35 | 1.51 | 1.15 | 1.12 | 28.9 | 46.5 |
| 576 | 0.17 | 7.49 | 1.96 | 0.84 | 1.94 | 0.81 | 0.39 | 0.20 | 15.3 | 49.0 |
| Spleen ||||||||||
| 24 | 0.51 | 62.0 | 2.92 | 0.93 | 0.87 | 0.15 | nd | nd | 67.4 | 92.0 |
| 60 | 0.60 | 84.4 | 4.17 | 1.85 | 2.19 | 1.39 | 0.62 | 0.51 | 96.9 | 87.0 |
| 120 | 0.26 | 90.0 | 5.98 | 2.63 | 3.65 | 1.61 | 0.94 | 1.62 | 106 | 83.8 |
| 168 | 0.87 | 94.0 | 6.20 | 2.54 | 3.24 | 1.15 | 0.63 | 0.39 | 109 | 85.9 |
| 384 | 0.12 | 26.6 | 2.75 | 1.48 | 2.40 | 1.40 | 1.26 | 1.20 | 43.1 | 61.6 |
| 576 | 0.08 | 26.6 | 1.78 | 0.71 | 1.18 | 0.56 | 0.42 | 0.51 | 32.7 | 81.3 |
| Back Skin ||||||||||
| 24 | 0.16 | 3.63 | nd | nd | nd | nd | nd | nd | 3.79 | 94.5 |
| 60 | 0.04 | 2.80 | 0.07 | 0.03 | 0.03 | nd | nd | nd | 2.96 | 95.0 |
| 120 | 0.03 | 4.63 | 0.16 | 0.06 | 0.06 | 0.02 | 0.01 | nd | 4.96 | 93.3 |
| 168 | 0.08 | 11.1 | 0.53 | 0.18 | 0.19 | 0.06 | 0.04 | 0.01 | 12.2 | 93.2 |
| 384 | 0.02 | 0.24 | 0.02 | nd | nd | nd | nd | nd | 0.26 | 88.7 |
| 576 | 0.01 | 0.09 | nd | nd | nd | nd | nd | nd | 0.10 | 89.5 |
| Hand Skin ||||||||||
| 24 | 0.14 | 13.6 | 0.23 | 0.03 | 0.04 | 0.02 | 0.02 | 0.01 | 14.1 | 96.4 |
| 60 | 0.13 | 23.9 | 0.68 | 0.20 | 0.11 | 0.09 | 0.06 | 0.03 | 25.2 | 94.2 |
| 120 | 0.17 | 24.6 | 0.92 | 0.22 | 0.29 | 0.08 | 0.04 | 0.03 | 26.4 | 93.3 |
| 168 | 0.32 | 25.7 | 1.02 | 0.27 | 0.39 | 0.17 | 0.21 | 0.07 | 28.3 | 92.2 |
| 384 | 0.13 | 13.54 | 1.11 | 1.46 | 0.47 | 0.11 | 0.05 | 0.04 | 17.02 | 79.6 |
| 576 | 0.10 | 1.10 | 0.13 | 0.06 | 0.16 | 0.03 | nd | nd | 1.56 | 70.5 |
| A & I Lymph Nodes ||||||||||
| 24 | 0.26 | 27.7 | 0.85 | 0.26 | 0.17 | 0.02 | nd | nd | 29.3 | 94.6 |
| 60 | 0.05 | 43.5 | 2.07 | 0.57 | 0.96 | 0.38 | 0.13 | nd | 47.6 | 91.2 |
| 120 | 0.24 | 68.2 | 4.16 | 1.61 | 3.10 | 1.08 | 0.23 | 0.07 | 78.7 | 86.6 |
| 168 | 1.03 | 42.4 | 4.05 | 2.03 | 2.99 | 1.30 | 0.41 | 0.36 | 55.4 | 77.0 |
| 384 | 0.26 | 29.7 | 2.33 | 0.99 | 1.85 | 0.61 | 0.61 | 0.46 | 39.2 | 75.8 |
| 576 | 0.23 | 14.6 | 0.79 | 0.28 | 0.55 | 0.26 | 0.26 | 0.14 | 18.0 | 81.1 |
| M & M Lymph Nodes ||||||||||
| 24 | 0.21 | 9.47 | 0.49 | 0.37 | 0.11 | 0.11 | 0.07 | 0.05 | 11.0 | 86.0 |
| 60 | 0.23 | 14.4 | 1.03 | 0.82 | 0.50 | 0.29 | 0.22 | 0.16 | 17.8 | 81.1 |
| 120 | 0.22 | 43.8 | 3.18 | 1.38 | 2.19 | 0.65 | 0.31 | 0.18 | 52.0 | 83.9 |
| 168 | 0.18 | 38.3 | 3.80 | 1.97 | 2.61 | 1.02 | 0.56 | 0.43 | 49.1 | 79.1 |
| 384 | 0.10 | 15.1 | 1.28 | 0.58 | 1.08 | 0.44 | 0.38 | 0.47 | 21.8 | 69.3 |
| 576 | 0.05 | 8.01 | 0.37 | 0.18 | 0.20 | 0.09 | 0.05 | 0.07 | 9.24 | 88.9 |
| Brain ||||||||||
| 24 | 0.06 | 2.21 | 0.03 | nd | nd | nd | nd | nd | 2.30 | 96.0 |
| 60 | 0.06 | 1.28 | 0.01 | nd | nd | nd | nd | nd | 1.35 | 92.5 |
| 20 | 0.06 | 0.94 | nd | nd | nd | nd | nd | nd | 1.00 | 94.2 |
| 168 | 0.05 | 2.27 | nd | nd | nd | nd | nd | nd | 2.32 | 97.6 |
| Colon ||||||||||
| 24 | 0.05 | 5.44 | 0.13 | 0.05 | 0.01 | 0.01 | 0.01 | 0.01 | 5.71 | 95.2 |
| 60 | 0.14 | 4.02 | 0.19 | 0.11 | 0.09 | 0.03 | 0.02 | nd | 4.65 | 86.3 |
| 120 | 0.03 | 6.88 | 0.65 | 0.35 | 0.39 | 0.05 | 0.01 | nd | 8.35 | 82.3 |
| 168 | 0.08 | 6.48 | 0.47 | 0.55 | 0.06 | 0.05 | 0.04 | 0.01 | 7.75 | 86.8 |
| Heart ||||||||||
| 24 | 0.04 | 10.3 | 0.28 | nd | nd | nd | nd | nd | 10.6 | 97.2 |

TABLE 15-continued

Average (n = 2) Tissue Concentrations (µg/g) of ISIS 2503 and All Detected Metabolites After 0.5 hr Intravenous Infusion of 10 mg/kg ISIS 2503 Encapsulated in Sterically Stabilized Liposomes to Rhesus Monkeys

| Time (hr) | (µg/mL) 2503 | n + 1 | n − 1 | n − 2 | n − 3 | n − 4 | n − 5 | n − 6 | Total | % Full Length |
|---|---|---|---|---|---|---|---|---|---|---|
| 60 | 0.12 | 6.28 | 0.20 | 0.06 | 0.06 | nd | nd | nd | 6.72 | 94.2 |
| 120 | 0.05 | 3.72 | 0.11 | nd | nd | nd | nd | nd | 3.89 | 95.8 |
| 168 | 0.07 | 2.78 | 0.10 | 0.05 | nd | nd | nd | nd | 2.99 | 91.3 |
| | | | | | Lung | | | | | |
| 24 | 0.14 | 22.5 | 0.44 | 0.20 | 0.03 | nd | nd | nd | 23.3 | 96.6 |
| 60 | 0.05 | 26.1 | 0.22 | 0.02 | nd | nd | nd | nd | 26.4 | 98.5 |
| 120 | 0.10 | 6.95 | 0.22 | nd | nd | nd | nd | nd | 7.28 | 93.8 |
| 168 | 0.19 | 4.45 | 0.09 | 0.03 | 0.02 | 0.01 | nd | nd | 4.79 | 90.5 |
| | | | | | Pancreas | | | | | |
| 24 | 0.11 | 3.63 | 0.14 | 0.20 | 0.35 | 0.36 | 0.72 | 0.60 | 9.41 | 41.2 |
| 60 | 0.12 | 5.53 | 0.30 | 0.13 | 0.30 | 0.19 | 0.44 | 0.63 | 10.6 | 54.6 |
| 120 | 0.09 | 2.62 | 0.16 | 0.12 | 0.27 | 0.35 | 0.24 | 0.46 | 4.75 | 53.8 |
| 168 | 0.07 | 1.78 | 0.25 | 0.33 | 0.09 | 0.06 | 0.30 | 0.55 | 3.46 | 53.2 |
| | | | | | Prostate | | | | | |
| 24 | 0.11 | 3.02 | 0.01 | 0.03 | nd | nd | nd | nd | 3.13 | 96.5 |
| 60 | 0.12 | 3.72 | 0.17 | 0.13 | nd | nd | nd | nd | 4.28 | 81.5 |
| 120 | 0.09 | 2.35 | 0.16 | 0.09 | 0.42 | 0.19 | 0.26 | 0.11 | 3.75 | 64.7 |
| 168 | 0.07 | 6.89 | 0.49 | 0.21 | 0.36 | 0.12 | 0.10 | 0.14 | 8.63 | 80.1 |
| | | | | | Ovary | | | | | |
| 24 | 0.09 | 5.18 | 0.20 | 0.16 | 0.13 | nd | nd | nd | 5.77 | 89.8 |
| 60 | 0.52 | 6.93 | 0.29 | 0.17 | 0.11 | 0.06 | 0.01 | 0.03 | 8.15 | 85.1 |
| 120 | 0.13 | 5.49 | 0.29 | 0.22 | 0.15 | 1.97 | 0.08 | 0.05 | 8.63 | 65.2 |
| 168 | 0.26 | 6.58 | 0.91 | 0.41 | 0.79 | 0.30 | 0.26 | 0.43 | 10.5 | 62.7 |

"nd" = not detected (detection level = 0.10 µg/mL)

TABLE 16

Estimated Tissue Pharmacokinetic parameters for ISIS 2503 (10 mg/kg) Encapsulated in Sterically Stabilized Liposomes Administered to Rhesus Monkeys by 0.5 hr Intravenous Infusion

| Tissue | $T_{1/2}$ (day) | MRT (day) | $T_{max}$ (day) | $C_{max}$ (µg/g) |
|---|---|---|---|---|
| Kidney Cortex | 11 | 15 | 1 | 23.3 |
| Kidney Medulla | 5.6 | 8.2 | 1 | 22.6 |
| Liver | 4.2 | 8.1 | 7 | 160 |
| A & I Lymph Node | NA[a] | 18 | 5 | 97.0 |
| M & M Lymph Node | 7.7 | 13 | 5 | 57.4 |
| Spleen | 9.7 | 14 | 5 | 107 |
| Back Skin | 3.1 | 7.0 | 7 | 16.5 |
| Hand Skin | 4.2 | 10 | 2 | 43.8 |
| Lung | 2.0 | 3.4 | 2 | 32.3 |
| Heart | 3.0 | 5.7 | 1 | 12.7 |
| Pancreas | 3.2 | 6.4 | 2 | 9.43 |
| Brain | NA | NA | 1 | 2.41 |
| Colon | NA | NA | 7[b] | 8.24 |
| Ovary | NA | NA | 2 | 6.92 |
| Prostate | NA | NA | 7[b] | 6.89 |

[a]"NA" = not available
[b]Concentration was still increasing at the last analyzed time point.

The appearance of metabolites was low even 576 hours after infusion (Table 15). Very low relative percentage of metabolites were observed for all the organs (~10–20%) except for the liver, the kidney cortex, and the pancreas (~30–60%). Higher concentration of oligonucleotide metabolites was observed as early as 24 hours after infusion in the pancreas. Although not wishing to be bound by any particular theory, this phenomenon could be related to the activity of lipases in this organ allowing more ISIS 2503 to escape from liposomes and be metabolized (McNeely et al., "Pancreas Function" In: *Clinical Chemistry: Theory, Analysis, and Correlation*, Kaplan and Pesce, eds., The C.V. Mosby Company, St. Louis, pp. 390–397, 1989). At later time points ($\geq$120 hr), increasing concentrations of chain-shortened oligonucleotide metabolites were seen in liver and kidney. Kidney and/or liver may also play a role in the degradation of liposomes but, alternatively, may be primary sites of free oligonucleotide and metabolite distribution.

In addition to chain-shortened metabolites, there were also UV absorbing peaks that migrated more slowly than parent oligonucleotide. Slower migrating oligonucleotide peaks have been identified for other phosphorothioate oligonucleotides in tissue. Slower migration suggests that the mass to charge ratio was increased either from the addition of a substituent or loss of charge. These metabolites are thought to represent intact drugs plus an additional substituent possibly an additional nucleotide or two (Griffey et al., *J. Mass. Spec.* 32:305, 1997). Thus, while not wishing to be bound by any particular theory, it is possible that the slower migrating peak observed in these studies is such a lengthened metabolite, and this peak is thus referred to as "n+1" in Table 15.

Toxicokinetic Summary and Conclusions: In this investigation, it has been demonstrated that ISIS 2503 in a sterically stabilized liposome formulation has a markedly prolonged circulation time. Maximum concentration ($C_{max}$) in blood is achieved at the end of infusion and it is approximately 90 µg/mL. Pharmacokinetic modeling of ISIS 2503 indicates a slow distribution process with a half-life of approximately 57 hours. The half-life of ISIS 2503 in this formulation is significantly greater than that observed for unencapsulated oligonucleotides suggesting that ISIS 2503 in liposomes is slowly distributed to tissues and protected from metabolism in blood. Unencapsulated oligonucleotide is cleared from plasma by a combination of metabolism and tissue distribution. Unencapsulated oligonucleotide has been reported to have half-lives ranging from 36–83 minutes. With this formulation there appears to be little metabolism, and clearance from blood is slow with a half-life of 57 hours. Clearly this formulation has altered the kinetics of circulating oligonucleotide. While not wishing to be bound by any particular theory, because tissue distribution is the primary route for both liposomal oligonucleotide and unencapsulated oligonucleotide clearance from circulation, slower kinetics of liposome uptake seen in tissue may explain the prolonged circulation of oligonucleotide in this study.

Liposomal ISIS 2503 is widely distributed into all tissues tested, in descending maximum concentration ($C_{max}$) order, liver> spleen> lymph nodes> hand skin> lung> kidney> back skin> heart> pancreas> colon> ovary> prostate> brain. Intact ISIS 2503 is the predominant oligonucleotide species measured indicating a slow metabolism in tissues and supporting the concept that liposomes remain intact in tissues. The apparent increase in metabolites observed in kidney, liver, and pancreas could be explained by digestion of the liposomes in these tissues, or preferential uptake of metabolites from circulation by these tissues. The high oligonucleotide concentrations in liver and spleen suggest that liposome formulations are primarily removed from blood by the reticulo-endothelial system. The persistence and abundance of intact ISIS 2503 in tissues is best explained by the protection from nucleases afforded by liposomal encapsulation.

Example 5

Evaluation of the Antitumor Activity of Sterically Stabilized Liposomes Comprising Antisense Oligonucleotides One advantage of some sterically stabilized liposomes is their ability to deliver conventional chemotherapeutic agents to tissues, particularly tumors, other than those of the reticuloendothelial system (RES) (Gabizon et al., *Proc. Natl. Acad. Sci. U.S.A.* 85:6949, 1988; Papahadjopoulos et al., *Proc. Natl. Acad. Sci. U.S.A.* 88:11460, 1991). In disease states where leaky vasculature is characteristic (e.g., inflammation, tumors), prolonging the circulation time via the liposomal oligonucleotide formulations of the invention may allow for more effective delivery of oligonucleotide as well as providing for a less frequent oligonucleotide dosing interval. In order to test the efficacy of liposomal oligonucleotide formulations against tumors, a human-mouse xenograft model was used.

A. Experimental Design and Methods

Liposomes: Sterically stabilized liposomes comprising $DSPE-MPEG_{2000}$ in the lipid phase and ISIS 2503 in the aqueous phase were prepared as in Example 3. ISIS 2503 loaded sterically stabilized liposomes comprising the monosialoganglioside $G_{M1}$ instead of $DSPE-MPEG_{2000}$ were prepared in like fashion, except that monosialoganglioside $G_{M1}$ (Sigma Chemical Co., St. Louis, Mo.) was substituted for $DSPE-MPEG_{2000}$ at the same final molar concentration. In some experiments, ISIS 13177 was used as a control. This phosphorothioate oligodeoxynucleotide has the nucleotide sequence 5'-TCAGTAATAGCCCCACATGG (SEQ ID NO: 26). In other experiments, ISIS 2105 was used as a control. This oligonucleotide has the nucleotide sequence 5'-TTGCTTCCATCTTCCTCGTC (SEQ ID NO: 27), which is targeted to the E2 gene of papillomavirus HPV-11. Saline formulations of ISIS 2503 were also included as controls in the experiments.

Xenografts: Xenografts of human tumor cell lines into BALB/c nude mice were performed essentially as described by Dean et al. (*Cancer Res.* 56:3499, 1996). Cell lines NCI-H69 and MIA PaCa-2 are available from the American Type Culture Collection (A.T.C.C., Rockville, Md.) as accession numbers ATCC HTB-119 and ATCC CRL-1420, respectively.

Dosing and Analysis: Formulations were administered intraperitoneally (i.p.) or intravenously (i.v.) at the indicated frequencies including every other day (q2d) and every third day (q3d). Tumor volume was measured at the indicated times by measuring perpendicular diameters and calculated as described Dean et al., *Cancer Res.* 56:3499, 1996). For distribution studies, mice were given two doses of 10 mg/kg of formulation and then sacrificed after 24 hours. Tumor tissue was removed and analyzed by capillary electrophoresis for the presence of various oligonucleotide species as described in Example 4.

B. Results

Distribution: Sterically stabilized liposomes comprising either $DSPE-MPEG_{2000}$ (PEG) or monosialoganglioside $G_{M1}$ (GM1) resulted in enhanced delivery of ISIS 2503 to H69 and Mia PaCa tumor cells (Tables 17 and 18, respectively). The enhanced delivery was observed both in terms of increased concentration and total amount of oligonucleotide delivered to tumor tissue, and as a percentage of the total dose of oligonucleotide administered to each animal. Of particular significance is the fact that significant improvements in the percentage of intact oligonucleotide delivered to the tumor tissue increased from less than about 4% (saline formulation) to about 11% (liposomes with $G_{M1}$) to over 15% (liposomes with PEG) (Table 18).

TABLE 17

Distribution of ISIS 2503 in Tumors in Mice with H69 Xenografts 24 Hours After Two Doses of 10 mg/kg

| Formu- | | Conc. (ug/g) | | Amount (ug) | | % of Dose | |
|---|---|---|---|---|---|---|---|
| lation | n[a] | Avg.[b] | SD[c] | Avg. | SD | Avg. | SD |
| Saline | 3 | 3.51 | 0.47 | 1.35 | 0.40 | 0.29 | 0.11 |
| Liposomes-PEG | 2 | 17.82 | 7.37 | 4.82 | 3.61 | 1.11 | 0.91 |
| Liposomes-GM1 | 2 | 10.01 | 3.24 | 5.40 | 3.85 | 3.08 | 2.08 |

[a]"n" = number of animals.
[b]"Avg." = average (mean)
"SD" = standard deviation.

TABLE 18

Distribution of ISIS 2503 in Tumors in Mice with MIA PaCa Xenografts 24 Hours After Two Doses of 10 mg/kg

| Formu- | | Conc. (µg/g) | | Amount (µg) | | % of Dose | |
|---|---|---|---|---|---|---|---|
| lation | n | Avg. | SD | Avg. | SD | Avg. | SD |
| A. Total concentration of ISIS 2503 & metabolites | | | | | | | |
| Saline | 3 | 3.82 | 1.96 | 3.74 | 2.32 | 0.09 | 0.06 |
| Liposomes-PEG | 3 | 16.21 | 4.98 | 15.27 | 10.93 | 0.36 | 0.25 |
| Liposomes-GM1 | 3 | 15.80 | 8.99 | 10.69 | 2.96 | 0.26 | 0.06 |
| B. Concentration of full-length ISIS 2503 | | | | | | | |
| Saline | 3 | 0.87 | 0.12 | 0.09 | 0.06 | 3.74 | 3.74 |
| Liposomes-PEG | 3 | 9.95 | 2.75 | 0.36 | 0.25 | 15.27 | 15.27 |
| Liposomes-GM1 | 3 | 8.56 | 5.18 | 0.26 | 0.06 | 10.69 | 10.69 |

TABLE 18-continued

Distribution of ISIS 2503 in Tumors in Mice with MIA
PaCa Xenografts 24 Hours After Two Doses of 10 mg/kg

| Formulation | n | Conc. (µg/g) | | Amount (µg) | | % of Dose | |
|---|---|---|---|---|---|---|---|
| | | Avg. | SD | Avg. | SD | Avg. | SD |

Antitumor Activity: The liposomal oligonucleotide formulations of the invention were evaluated for their ability to control the growth of human tumor cells transplanted BALB/c nude mice. One such experiment, in which liposomes comprising ISIS 2105 were used as a control formulation, is shown in Table 19.

TABLE 19

Antitumor Activity of Liposomal Formulations
of ISIS 2503 Against MIA PaCa Xenografts

| Formulation: | Day | n | Tumor Size (mm³) | | |
|---|---|---|---|---|---|
| | | | Mean | SD | Std. Error |
| Saline/no oligonucleotide | | | | | |
| | 10 | 8 | 0.115 | 0.036 | 0.013 |
| | 14 | 8 | 0.321 | 0.119 | 0.042 |
| | 21 | 8 | 0.964 | 0.417 | 0.148 |
| | 30 | 8 | 1.544 | 0.708 | 0.250 |
| PEG-Liposome/ISIS 2503 (1 mg/kg) | | | | | |
| | 10 | 7 | 0.116 | 0.033 | 0.012 |
| | 14 | 7 | 0.216 | 0.101 | 0.038 |
| | 21 | 7 | 0.700 | 0.335 | 0.127 |
| | 30 | 7 | 1.480 | 0.851 | 0.322 |
| PEG-Liposome/ISIS 2503 (5 mg/kg) | | | | | |
| | 10 | 4 | 0.090 | 0.008 | 0.004 |
| | 14 | 4 | 0.208 | 0.036 | 0.018 |
| | 21 | 4 | 0.550 | 0.153 | 0.077 |
| | 30 | 4 | 0.998 | 0.345 | 0.173 |
| PEG-Liposome/ISIS 2503 (25 mg/kg) | | | | | |
| | 10 | 6 | 0.102 | 0.047 | 0.019 |
| | 14 | 6 | 0.142 | 0.084 | 0.034 |
| | 21 | 6 | 0.283 | 0.172 | 0.070 |
| | 30 | 6 | 0.603 | 0.331 | 0.135 |
| PEG-Liposome/ISIS 2105 (25 mg/kg) | | | | | |
| | 10 | 5 | 0.120 | 0.038 | 0.017 |
| | 14 | 5 | 0.294 | 0.180 | 0.081 |
| | 21 | 5 | 0.996 | 0.735 | 0.329 |
| | 30 | 5 | 1.508 | 0.981 | 0.439 |

TABLE 20

Antitumor Activity of Liposomal Formulations
of ISIS 2503 Against NCI-H69 Xenografts

| Formulation: | Day | n | Tumor Size (mm³) | | |
|---|---|---|---|---|---|
| | | | Mean | SD | Std. Error |
| Saline[a]/no oligonucleotide | | | | | |
| | 21 | 7 | 0.150 | 0.061 | 0.023 |
| | 28 | 7 | 0.513 | 0.493 | 0.186 |
| | 35 | 7 | 0.749 | 0.392 | 0.148 |
| | 42 | 7 | 2.106 | 2.277 | 0.861 |
| Saline[a]/ISIS 2503 (25 mg/kg) | | | | | |
| | 21 | 7 | 0.163 | 0.056 | 0.021 |
| | 28 | 7 | 0.334 | 0.205 | 0.077 |
| | 35 | 7 | 0.766 | 0.545 | 0.206 |
| | 42 | 7 | 1.021 | 0.751 | 0.284 |
| PEG-Liposome[b]/ISIS 2503 (25 mg/kg) | | | | | |
| | 21 | 6 | 0.150 | 0.068 | 0.028 |
| | 28 | 6 | 0.222 | 0.121 | 0.049 |
| | 35 | 6 | 0.417 | 0.251 | 0.102 |
| | 42 | 6 | 0.753 | 0.551 | 0.225 |
| PEG-Liposome[b]/ISIS 13177 (25 mg/kg) | | | | | |
| | 21 | 7 | 0.163 | 0.043 | 0.016 |
| | 28 | 7 | 0.460 | 0.233 | 0.088 |
| | 35 | 7 | 0.956 | 0.410 | 0.155 |
| | 42 | 7 | 1.636 | 1.037 | 0.392 |

[a]Saline formulations given qd.
[b]liposomal formulations given q3d.

In the experiment described in Table 19, sterically stabilized liposomes comprising DPSE-MPEG$_{2000}$ and ISIS 2503 were given in doses of 1, 5 and 25 mg/kg. Controls included a saline solution (0.90% NaCl) and sterically stabilized liposomes comprising ISIS 2105. Dosing was i.v. q3d. As can be seen in Table 19, treatment with sterically stabilized liposomes comprising ISIS 2503 resulted in a dose-dependent reduction in the rate of tumor growth. At day 21, tumor sizes averaged 0.964 and 0.996 mm³ for the animals treated with, respectively, saline and liposomal ISIS 2105. In contrast, animals treated with liposomal ISIS 2503 at 1, 5 and 25 mg/kg had tumors averaging 0.700, 0.550 and 0.283 mm³, respectively.

A similar experiment (Table 20) shows that the liposomal oligonucleotide formulation is also effective against NCI-H69-derived xenografts. In this experiment, animals treated with 25 mg/kg of ISIS 2503 given as part of a liposomal formulation had tumors averaging 0.417 mm³ in size on day 35, as compared to 0.749 and 0.766 mm³ for saline alone and saline formulated oligonucleotide, respectively. Treatment with a liposomal formulation comprising a control oligonucleotide (ISIS 13177) at 25 mg/kg resulted in tumors averaging 0.956 mm³ on day 35.

The above results demonstrate that sterically stabilized liposomal oligonucleotide formulations have several advantages over traditional formulations. First, the liposomal formulations of the invention result in improved pharmacodynamic properties (e.g., prolonged clearance time from the blood, enhanced biostability in blood and kidney samples, etc.) that result in greater circulating concentrations and stability of full-length oligonucleotides. Second, the liposomal formulations of the invention result in enhanced delivery, relative to traditional saline formulations, of the oligonucleotides encompassed thereby to tumor tissues. Third, due at least in part to the above features, liposomal oligonucleotide formulations can achieve higher concentrations and greater specific effects attributable to antisense oligonucleotides using a less frequent dosing regime than seen with traditional formulations (e.g., as seen from the data in Table 20, 25 mg/kg of ISIS 2503 given every third day in a liposomal formulation was more effective than the same dose of ISIS 2503 given daily in saline). Taken together, these properties are expected to result in an efficacious method for treating an animal, including a human, suffering from a hyperproliferative disease or disorder such as cancer.

What is claimed is:

1. A pharmaceutical composition comprising a sterically stabilized liposome and one or more antisense oligonucleotides targeted to a translation initiation codon or codon 12 of an H ras gene.

2. A pharmaceutical composition comprising a sterically stabilized liposome and one or more oligonucleotides comprising from about 8 to about 30 nucleotides, wherein one of said oligonucleotides is ISIS 2503 having the sequence of SEQ ID NO: 2.

3. A method of inhibiting the expression of a ras gene comprising contacting cells, tissues, organs or organisms expressing said ras gene with the pharmaceutical composition of claim 1.

4. A method of inhibiting the growth of cells comprising contacting said cells with the pharmaceutical composition of claim 1.

* * * * *